US012601734B2

(12) United States Patent
Leung et al.

(10) Patent No.: US 12,601,734 B2
(45) Date of Patent: Apr. 14, 2026

(54) METHODS AND USES OF ENZYMATIC LABELING OF ADP-RIBOSE CONTAINING MOLECULES

(71) Applicants: THE JOHNS HOPKINS UNIVERSITY, Baltimore, MD (US); COLD SPRING HARBOR LABORATORY, Cold Spring Harbor, NY (US)

(72) Inventors: Anthony K. L. Leung, Ellicott City, MD (US); Yoshinari Ando, Baltimore, MD (US); Robert L McPherson, Baltimore, MD (US); Mohsen Badiee, Baltimore, MD (US); Elad Elkayam, Cold Spring Harbor, NY (US)

(73) Assignees: THE JOHNS HOPKINS UNIVERSITY, Baltimore, MD (US); COLD SPRING HARBOR LABORATORY, Cold Spring Harbor, NY (US)

( * ) Notice: Subject to any disclaimer, the term of this patent is extended or adjusted under 35 U.S.C. 154(b) by 1390 days.

(21) Appl. No.: 17/044,913

(22) PCT Filed: Apr. 2, 2019

(86) PCT No.: PCT/US2019/025323
§ 371 (c)(1),
(2) Date: Oct. 2, 2020

(87) PCT Pub. No.: WO2019/195240
PCT Pub. Date: Oct. 10, 2019

(65) Prior Publication Data

US 2021/0156847 A1 May 27, 2021

Related U.S. Application Data

(60) Provisional application No. 62/651,444, filed on Apr. 2, 2018.

(51) Int. Cl.
*G01N 33/533* (2006.01)
*C07H 21/00* (2006.01)
(Continued)

(52) U.S. Cl.
CPC ........... *G01N 33/533* (2013.01); *C07H 21/00* (2013.01); *C07K 9/00* (2013.01); *C12P 19/30* (2013.01);
(Continued)

(58) Field of Classification Search
CPC ........ G01N 33/533; C07H 21/00; C07K 9/00; C12P 19/30; C12P 19/34; C12P 21/005; C12Q 1/6811
See application file for complete search history.

(56) References Cited

U.S. PATENT DOCUMENTS

| | | | |
|---|---|---|---|
| 2011/0104717 | A1 | 5/2011 | Fantl et al. |
| 2014/0128286 | A1 | 5/2014 | Khabar |
| 2014/0170643 | A1 | 6/2014 | Yu |

FOREIGN PATENT DOCUMENTS

| | | | |
|---|---|---|---|
| FR | 2505845 | A1 | 5/1981 |
| WO | 2012153187 | A2 | 11/2012 |

OTHER PUBLICATIONS

Alvarez-Gonzalez, R. et al., "Characterization of Polymers of Adenosine Diphosphate Ribose Generated in Vitro and in Vivo", Biochemistry, 1987, pp. 3218-3224, vol. 26.

(Continued)

*Primary Examiner* — Jezia Riley
(74) *Attorney, Agent, or Firm* — MH2 Technology Law Group LLP

(57) ABSTRACT

Described is ELTA (Enzymatic Labeling of Terminal ADP-ribose) to label free, protein-conjugated, or nucleic acid-conjugated ADP-ribose monomer and polymers at their 2'-OH termini. When coupled with different chemical ana-
(Continued)

logs, ELTA can be used for various applications including fluorescence-based biophysical measurement of PAR-protein interaction, detection of PAR length from cells, and enrichment of ADP-ribosylated peptides for mass spectrometry identification.

28 Claims, 11 Drawing Sheets

(51) Int. Cl.
*C07K 9/00* (2006.01)
*C12P 19/30* (2006.01)
*C12P 19/34* (2006.01)
*C12P 21/00* (2006.01)
*C12Q 1/6811* (2018.01)

(52) U.S. Cl.
CPC ............ *C12P 19/34* (2013.01); *C12P 21/005* (2013.01); *C12Q 1/6811* (2013.01)

(56) References Cited

OTHER PUBLICATIONS

Ando, Y. et al., "ELTA: Enzymatic Labeling of Terminal ADP-Ribose", Molecular Cell, 2019, pp. 845-856, vol. 73, Elsevier Inc.
Bagshaw, C., "ATP analogues at a glance", Cell Science at a Glance, 2011, pp. 459-460.
Barkauskaite, E., Y. et al., "Structures and Mechanisms of Enzymes Employed in the Synthesis and Degradation of PARP-Dependent Protein ADP-Ribosylation", Molecular Cell, 2015, pp. 935-946, vol. 58, Elsevier Inc.
Berger, N. et al., "Opportunities for the repurposing of PARP inhibitors for the therapy of non-oncological diseases", British Journal of Pharmacology, 2018, pp. 192-222, vol. 175.
Bock, F. et al., "RNA regulation by Poly(ADP-ribose) polymerase", Mol Cell. 2015, pp. 959-969, vol. 58, No. 6, doi:10.1016/j.molcel.2015.01.037.
Cayley, J. et al., "Synthesis, Characterisation and Biological Significance of (2-5) Oligoadenylate Derivatives of NAD+, ADP-Ribose and Adenosine(5)Tetraphospho(5)Adenosine", Eur. J. Biochem. 1982, pp. 601-608, vol. 122.
Chen, H. et al., "What have single-molecule studies taught us about gene expression", Genes Development, 2016, pp. 1796-1810, vol. 30, Published by Cold Spring Harbor Laboratory Press; ISSN 0890-9369/16; www.genesdev.org.
Daniels, C. et al., "The Promise of Proteomics for the Study of ADP-ribosylation", Mol Cell., 2015, pp. 911-924, vol. 58, No. 6 doi: 10.1016/j.molcel.2015.06.012.
Darosa, P. et al., "Allosteric Activation of the RNF146 Ubiquitin Ligase by a Poly(ADP-ribosyl)ation Signal", Nature, 2015, pp. 223-226, vol. 517, No. 7533, doi:10.1038/nature13826.
Fahrer, J. et al., "High affinity interaction of poly(ADP-ribose) and the human DEK oncoprotein depends upon chain length+", Biochemistry, 2010, pp. 7119-7130, vol. 49, No. 33, doi:10.1021/bi1004365.
Fahrer, J. et al., "Quantitative analysis of the binding affinity of poly(ADP-ribose) to specific binding proteins as a function of chain length", Nucleic Acids Research, 2007, pp. 1-9, vol. 35, No. 21, doi:10.1093/nar/gkm944.
Feijs, K. et al., "Expanding functions of intracellular resident mono-ADP-ribosylation in cell physiology", the FEBS Journal, 2013, pp. 3519-3529, vol. 280.
Feijs, K. et al., "Macrodomain-containing proteins: regulating new intracellular functions of mono(ADP-ribosyl)ation", Nature Reviews, Molecular Cell Biology, 2013, pp. 443-452, vol. 13.
Ferbus, D. et al., "THE 2" 5" Oligoadenylate Synthetase Has a Multifunctional 2" 5" Nucleotidyl-Transferase Activity", Biochemical and Biophysical Research Communications, 1981, pp. 847-856, vol. 100, No. 2.
Gibson, B. et al., "Generation and Characterization of Recombinant Antibody-like ADP-Ribose Binding Proteins", Biochemistry, 2017, pp. 6305-6316, vol. 56.
Gupte, R. et al., "PARPs and ADP-ribosylation: recent advances linking molecular functions to biological outcomes", Genes Development, 2017, pp. 101-126, vol. 31.
Hottiger, M., "Nuclear ADP-Ribosylation and Its Role in Chromatin Plasticity, Cell Differentiation, and Epigenetics", Annu. Rev. Biochem., 2015, pp. 227-263, vol. 84.
Hottiger, M., "Toward a unified nomenclature for mammalian ADP-ribosyltransferases", Trends in Biochemical Sciences, 2010, pp. 208-219, vol. 35, No. 4.
James, D. et al., "First-in-Class Chemical Probes against Poly(ADP-ribose) Glycohydrolase (PARG) Inhibit DNA Repair with Differential Pharmacology to Olaparib", ACS Chem. Biol. , 2016, pp. 3179-3190, vol. 11.
Jewett, J. et al., "Cu-free click cycloaddition reactions in chemical biology", Chem Soc Rev., 2010, pp. 1272-1279, vol. 39, No. 4.
Juarez-Salinas, H. et al., "Poly(ADP-ribose) levels in carcinogen-treated cells", Nature, 1979, pp. 740-741, vol. 282.
Justesen, J. et al., "Elongation mechanism and substrate specificity of 2",5"-oligoadenylate synthetase", Proc. Natl. Acad. Sci. USA, 1980, pp. 4618-4622, vol. 77, No. 8.
Justesen, J. et al., "Gene structure and function of the 2"-5"-oligoadenylate synthetase family", CMLS, Cell. Mol. Life Sci., 2000, pp. 1593-1612, vol. 57.
Kanai, M. et al., "Presence of Branched Portion in Poly(Adenosine Diphosphate Ribose) in Vivo*", The Hournal Of Biological Chemistry, 1982, pp. 6217-6223, vol. 257, No. 11.
Kang, H. et al., " Iduna is a poly(ADP-ribose) (PAR)-dependent E3 ubiquitin ligase that regulates DNA damage", PNAS, 2011, pp. 14103-14108, vol. 108, No. 34.
Keith, G. et al., "Use of Two-Dimensional Thin-Layer Chromatography for the Components Study of Poly(adenosine diphosphate ribose)", Analytical Biochemistry, 1990, pp. 309-313, vol. 191.
Kraus, L. et al., "PARP-1 and gene regulation: Progress and puzzles", Molecular Apects of Medicine, 2013, pp. 1109-1123, vol. 34.
Kristiansen, H. et al., "The Oligoadenylate Synthetase Family: An Ancient Protein Family with Multiple Antiviral Activities", Journal of Interferon Cytokine Research, 2011, pp. 41-48, vol. 31, No. 1.
Krukenberg, K. et al., "Extracellular poly(ADP-ribose) is a pro-inflammatory signal for macrophages", Chem Biol., 2015, vol. 22, No. 4, pp. 446-452, doi:10.1016/j.chembiol.2015.03.007.
Lambrecht, M. et al., "Synthesis of Dimeric ADP-Ribose and Its Structure with Human Poly(ADP-ribose) Glycohydrolase", JACS, 2015, pp. 3558-3564, vol. 137.
Leung, A. et al., "Poly(ADP-ribose) Regulates Stress Responses and microRNA Activity in the Cytoplasm", Mol Cell. , 2011, vol. 42, No. 4, pp. 489-499, doi:10.1016/j.molcel.2011.04.015.
Leung, A., "PARPs", Current Biology, 2017. pp. R1246-R1248, vol. 27.
Lord, C. et al., "PARP inhibitors: Synthetic lethality in the clinic", Science, 2017, pp. 1-6, vol. 355, No. 1152-1158.
Martello, R. et al., "Quantification of cellular poly(ADP-ribosyl)ation by stable isotope dilution mass spectrometry reveals tissue- and drugdependent stress response dynamics", ACS Chem Biol., 2013, vol. 8, No. 7, pp. 1567-1575, doi:10.1021/cb400170b.
Mcpherson, R. et al., "ADPr-ChAP: Mapping ADP-Ribosylation onto the Genome", Molecular Cell, 2016, pp. 326-3.27, vol. 61.
Min, W. et al., "Poly(ADP-ribose) binding to Chk1 at stalled replication forks is required for S-phase checkpoint activation", Nature Communications, pp. 1-14, vol. 4, No. 2993.
Palazzo, et al., "ADP-ribosylation: new facets of an ancient modification", FEBS J., 2017, vol. 18, pp. 2932-2946.
Palazzo, et al., "Processing of protein ADP-ribosylation by Nudix hydrolases", Biochem J., 2015 vol. 468, No. 2, pp. 293-301.
Pascal, et al., "The rise and fall of poly(ADP-ribose): An enzymatic perspective", DNA Repair (Amst)., 2015, vol. 32, pp. 10-16.
Popp, et al., "Site-specific non-covalent interaction of the biopolymer poly(ADP-ribose) with the Werner syndrome protein regulates protein functions", ACS Chem Biol., 2013, vol. 8, No. 1, pp. 179-188.

(56) References Cited

OTHER PUBLICATIONS

Rippmann, J. et al., "Functional Characterization of the Poly(ADP-ribose) Polymerase Activity of Tankyrase 1, a Potential Regulator of Telomere Length", J. Mol. Biol., 2002, pp. 217-224, vol. 323.
Rouleau, M. et al., "PARP inhibition: PARP1 and beyond", Nat Rev Cancer. 2010, pp. 293-301, vol. 10, No. 4, doi:10.1038/nrc2812.
Shah, G. et al., "Methods for Biochemical Study of Poly(ADP-Ribose) Metabolism in Vitro and in Vivo", Analytical Biochemistry, 1995, pp. 1-13, vol. 227.
Slade, D. et al., "The structure and catalytic mechanism of a poly(ADP-ribose) glycohydrolase", Nature, 2011, pp. 616-620, vol. 477, No. 7366.
Tan, E. et al., "Large scale preparation and characterization of poly(ADP-ribose) and defined length polymers", Anal Biochem., 2012, pp. 126-136, vol. 428, No. 2, doi:10.1016/j.ab.2012.06.015.
Wang, Z. et al., "Recognition of the iso-ADP-ribose moiety in poly(ADP-ribose) by WWE domains suggests a general mechanism for poly(ADP-ribosylation-dependent ubiquitination", Genes Development, 2012, pp. 235-240, vol. 26.
Wienken, C. et al., "Protein-binding assays in biological liquids using microscale thermophoresis", Nature Communications, 2010, pp. 1-7, vol. 1, No. 100, DOI: 10.1038/ncomms1093 | www.nature.com/naturecommunications.
Yuan, Z. et al., "PARP inhibitors as antitumor agents: a patent update (2013-2015)", Expert Opinion on Therapeutic Patents, vol. 27 No. 3, pp. 363-382, DOI: 10.1080/13543776.2017.1259413.
Zhang, F. et al., "The oligonucleotide/oligosaccharide-binding fold motif is a poly(ADP-ribose)-binding domain that mediates DNA damage response", PNAS, May 20, 2014, pp. 7278-7283, vol. 111, No. 20.
Zhang, Y. et al., "RNF146 is a poly(ADP-ribose)-directed E3 ligase that regulates axin degradation and Wnt signalling", Nature Cell Biology, 2011, pp. 623-639, vol. 13, No. 5.
Jiang, H., et al., "Clickable NAD Analogues for Labeling Substrate Proteins of Poly(ADP-ribose) Polymerases" J Am Chem Soc. Jul. 14, 2010; 132(27): 9363-9372. doi:10.1021/ja101588r.
Daniels, et al., Nudix hydrolases degrade protein-conjugated ADP-ribose. Sci Rep. 2015; 5: 18271.
Leung, Poly(ADP-ribose): an organizer of cellular architecture. J Cell Biol. Jun. 9, 2014;205(5):613-9.
Vivelo, C., et al., "Proteomics Approaches to Identify Mono(ADP-ribosyl)ated and Poly(ADP-ribosyl)ated proteins" Proteomics. Jan. 2015 ; 15(0): 203-217. doi:10.1002/pmic.201400217.
Poulsen, J., et al., "Enzyme assays for synthesis and degradation of 2-5as and other 2'-5' oligonucleotides" BMC Biochemistry (2015) 16:15.
Hornung, et al., OAS proteins and cGAS: unifying concepts in sensing and responding to cytosolic nucleic acids. Nat Rev Immunol. Aug. 2014;14(8):521-8.
Aboul-Ela, et al., Labeling methods for the study of poly- and mono(ADP-ribose) metabolism in cultured cells. Anal Biochem. Oct. 1988;174(1):239-50.

| | 1 | 2 | 3 | 4 | 5 | 6 | A260 |
|---|---|---|---|---|---|---|---|
| ADPr | - | - | + | + | - | - | 1.252 |
| NAD+ | - | - | - | - | + | - | 1.237 |
| isoADPr | - | - | - | - | - | + | 1.564 |
| OAS1 | - | + | + | + | + | + | |
| POLY(I:C) | - | + | - | + | + | + | |
| $^{32}$P-dATP | + | + | + | + | + | + | |

NAD+ iso-ADP-ribose $R_1$ =H OR (ADP-ribose)$_n$, WHERE n ≥1

$R_2$ =N, Cy3 OR Cy5 MOIETIES $R_3$ =H, Cy5, BIOTIN, OR AZIDO MOIETIES

* = $^{32}$P

METHODS AND USES OF ENZYMATIC LABELING OF ADP-RIBOSE CONTAINING MOLECULES

CROSS-REFERENCE TO RELATED APPLICATIONS

This application is a 35 U.S.C. § 371 U.S. national entry of International Application PCT/US2019/025323, having an international filing date of Apr. 2, 2019, which claims the benefit of U.S. Provisional Application No. 62/651,444, filed Apr. 2, 2018, the content of each of the aforementioned applications is herein incorporated by reference in their entirety.

STATEMENT OF GOVERNMENTAL INTEREST

This invention was made with government support under grant no. R01-GM104135 awarded by the National Institutes of Health. The government has certain rights in the invention.

BACKGROUND OF THE INVENTION

ADP-ribosylation involves the transfer of ADP-ribose from $NAD^+$ onto proteins post-translationally in unicellular and multicellular organisms. ADP-ribose can be added singly as mono(ADP-ribose) (MAR) or in polymeric form as poly(ADP-ribose) (PAR) by ADP-ribosyltransferases, including a family of enzymes commonly known as poly (ADP-ribose) polymerase (PARPs). ADP-ribosylation can be reversed by macrodomain-containing enzymes, including poly(ADP-ribose) glycohydrolase (PARG). ADP-ribosylation has been implicated in DNA damage, transcription, chromatin structure, non-membranous structure formation, host-pathogen interactions and RNA metabolism. Dysregulation of ADP-ribosylation or PARP activity has been implicated in the pathogenesis of diseases including cancers, virus infection and neurodegeneration. Inhibitors of certain PARP family members have already shown promise in treating ovarian, prostate, breast and other cancers, with three drugs approved by FDA. In addition, these inhibitors showed potential for repurposing in non-oncological diseases. There is, however, still much to be learnt about the structure, interaction, and biology of this therapeutically important modification, where progress has been hampered by a lack of tools.

Besides being a protein modification, PAR is also a polynucleotide chemically similar to DNA or RNA. The measurement, detection and enrichment of DNA/RNA in vitro and from cells have been made possible by modifying nucleic acids by enzymes with tags (e.g., fluorophore, radioactive phosphate or biotin) at either terminus. However, the lack of similar bioconjugation technology for PAR makes it difficult to adapt existing molecular biology techniques to investigate this polynucleotide. ADP-ribose has two ribose moieties: one as part of an adenosine group and a non-adenosine ribose that exists in an equilibrium between a closed and open chain, the latter of which possesses an aldehyde group at its 1" position (FIG. 1*a*, red). The aldehyde group is chemically reactive and can conjugated to either protein or another ADP-ribose to form PAR. It has previously been shown that this 1" aldehyde group can also be used for end-labeling by conjugating to carbonyl-reactive biotin analogs via chemical reactions[16]. However, as such, this aldehyde group is unavailable in ADP-ribosylated proteins for labeling, and there have been no methods to label protein-conjugated ADP-ribose.

SUMMARY OF THE INVENTION

One embodiment of the present invention is ELTA (Enzymatic Labeling of Terminal ADP-ribose) to label free, protein-conjugated, or nucleic acid-conjugated ADP-ribose monomer and polymers at their 2'-OH termini. The inventors demonstrated that ELTA is a sensitive approach to label and assess the length of PAR isolated in vitro and from cells. When coupled with different chemical analogs, ELTA can be used for various applications including fluorescence-based biophysical measurement of PAR-protein interaction and enrichment of ADP-ribosylated peptides for mass spectrometry identification of endogenous and in vitro substrates.

One embodiment of the present invention is a method of labeling ADP-ribose. The method comprises the steps of providing a monomer or polymer of ADP-ribose; incubating the monomer or polymer of ADP-ribose with an enzyme and a label; and forming a monomer or polymer of ADP-ribose labeled at the 2'OH terminus. The ADP-ribose maybe a monomer or a polymer, a branched polymer, or a combination thereof. A suitable sized ADP-ribose may have 100 or more ADP-ribose subunits or less than 100 ADP-ribose subunits, as examples. Enzymes that add label to the 2' OH terminus are suitable for the methods of the present invention. An example is 2'-5'-Oligoadenylate Synthetase (OAS) that is a group of enzymes including OAS1, OAS2, OAS3, 2'-5' Oligoadenylate Synthetase-Like protein (OASL), their sequence and structural homologues, or a combination thereof. Suitable labels used in the present invention include a label of Formula VII:

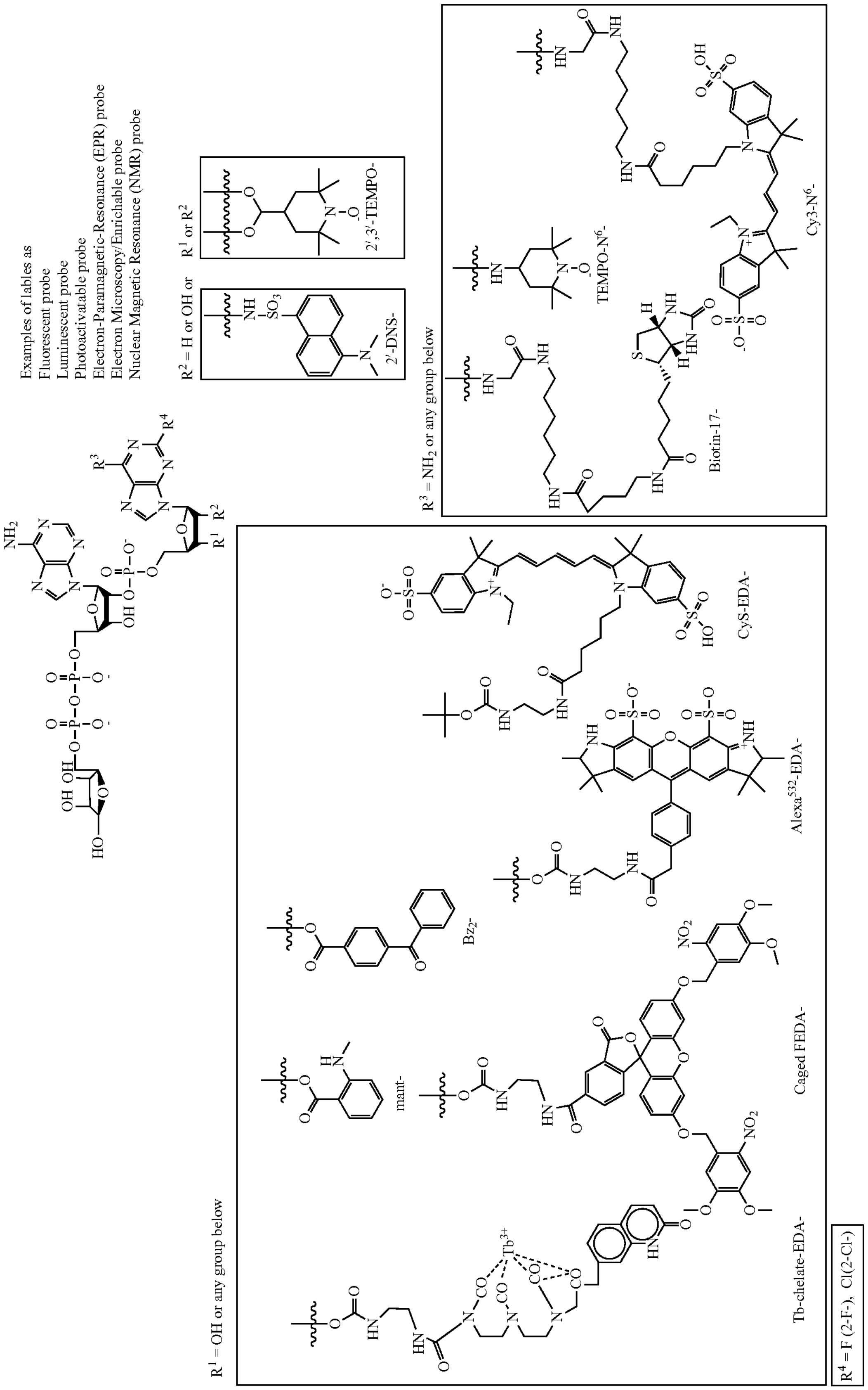

Examples of lables as
Fluorescent probe
Luminescent probe
Photoactivatable probe
Electron-Paramagnetic-Resonance (EPR) probe
Electron Microscopy/Enrichable probe
Nuclear Magnetic Resonance (NMR) probe $R^2$ = H or OH or

2'-DNS- $R^1$ or $R^2$

2',3'-TEMPO- $R^3$ = $NH_2$ or any group below

Biotin-17-

TEMPO-$N^6$-

Cy3-$N^6$-

$R^1$ = OH or any group below

Tb-chelate-EDAmant-

Caged FEDA- $Bz_2$-

Alexa$^{532}$-EDA-

Cy5-EDA- $R^4$ = F (2-F-), Cl(2-Cl-)

Some of the methods of the present produce a monomer or polymer of ADP-ribose labeled at the 2'OH terminus having the structure of Formula I:

wherein R1 is H or (ADP-ribose) n, wherein n≥1; R2 is N, a Cy3 moiety, a Cy5 moiety; and R3 is H, a Cy5, a Biotin, or an Azido moiety; and where P* is P or $^{32}$P.

(I)

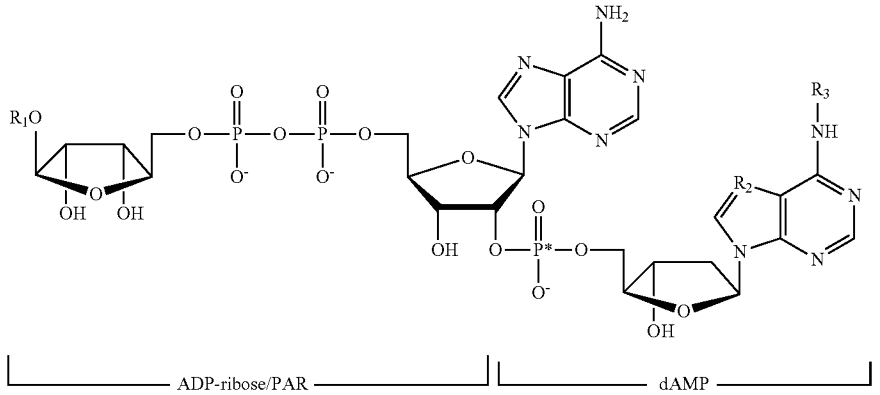

$R_1$ = H or (ADP-ribose)$_n$, where n ≥ 1
$R_2$ = N, Cy3 or Cy5 moieties
$R_3$ = H, Cy5, Biotin, or Azido moieties
* = $^{32}$P wherein R1 is H or (ADP-ribose)n, wherein n≥1; R2 is N, a Cy3 moiety, a Cy5 moiety; and R3 is H, a Cy5, a Biotin, or an Azido moiety; and where P* is P or $^{32}$P. Methods of the present invention may produce a monomer or polymer of ADP-ribose labeled at the 2'OH terminus having the structure of Formula V:

ADP-ribose/PAR-X (V)

wherein X is a label of Formula VII.

Any suitable monomer or polymer of ADP-ribose may be used in the present invention including cellular extracts including a monomer or polymer of ADP-ribose (in vitro ADP-ribose) or monomers or polymers of ADP-ribose present within cells (in vivo ADP-ribose).

Another embodiment of the present invention is a compound of Formula I;

Another embodiment of the present invention is a method for labeling ADP-ribose. The method comprises: providing a protein attached to a monomer or a polymer of ADP-ribose; incubating the protein attached to a monomer or a polymer of ADP-ribose with an enzyme and a label; forming a protein attached to the monomer or polymer of ADP-ribose labeled at the 2'OH terminus. Suitable proteins include those attached to a monomer of ADP-ribose, a polymer of ADP-ribose, a branch polymer of ADP-ribose, or a combination thereof. The attached ADP-ribose may have 100 or more ADP-ribose subunits or less than 100 ADP-ribose subunits, as examples. The methods of the present invention may produce a protein attached to the monomer or the polymer of ADP-ribose labeled at the 2'OH terminus having structure of formula II, formula III, or formula IV:

(I)

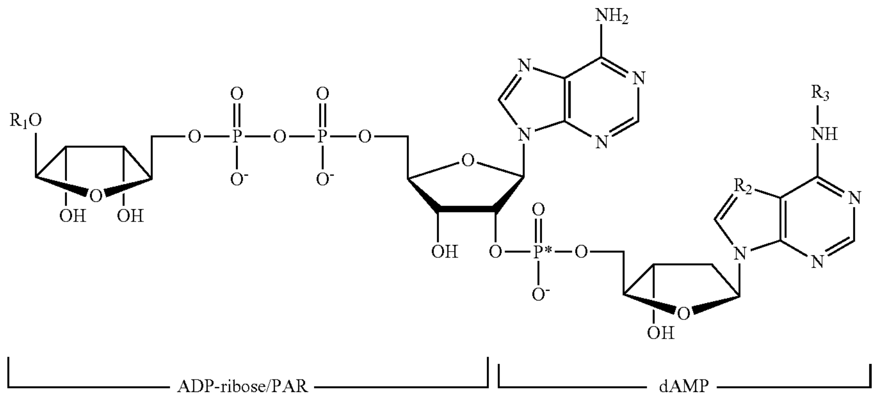

(II)
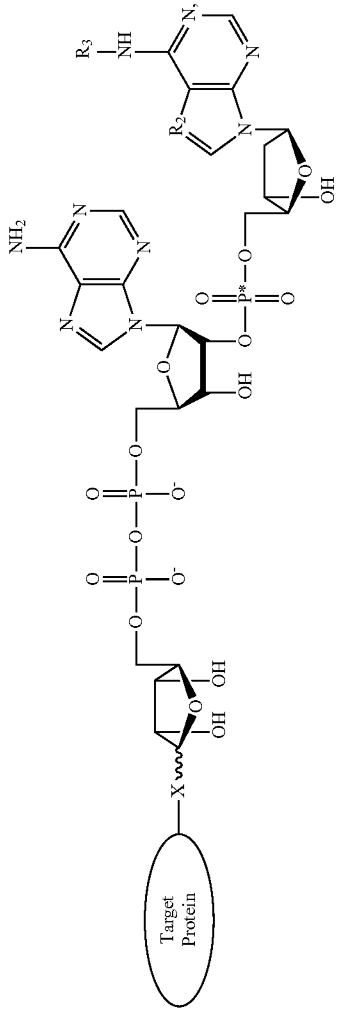
Mono(ADP-ribosyl)ated protein
(III)
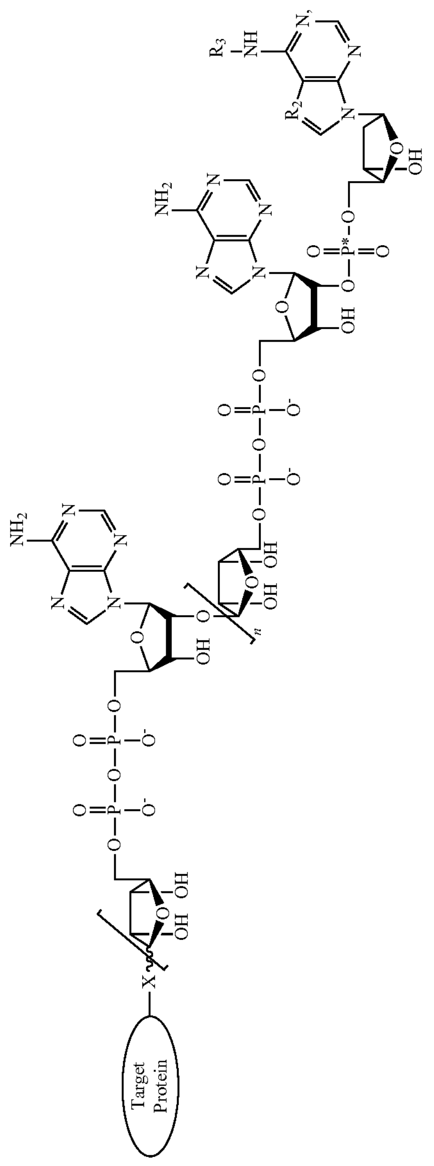
Poly(ADP-ribosyl)ated protein (with linear chain)

-continued
(IV)
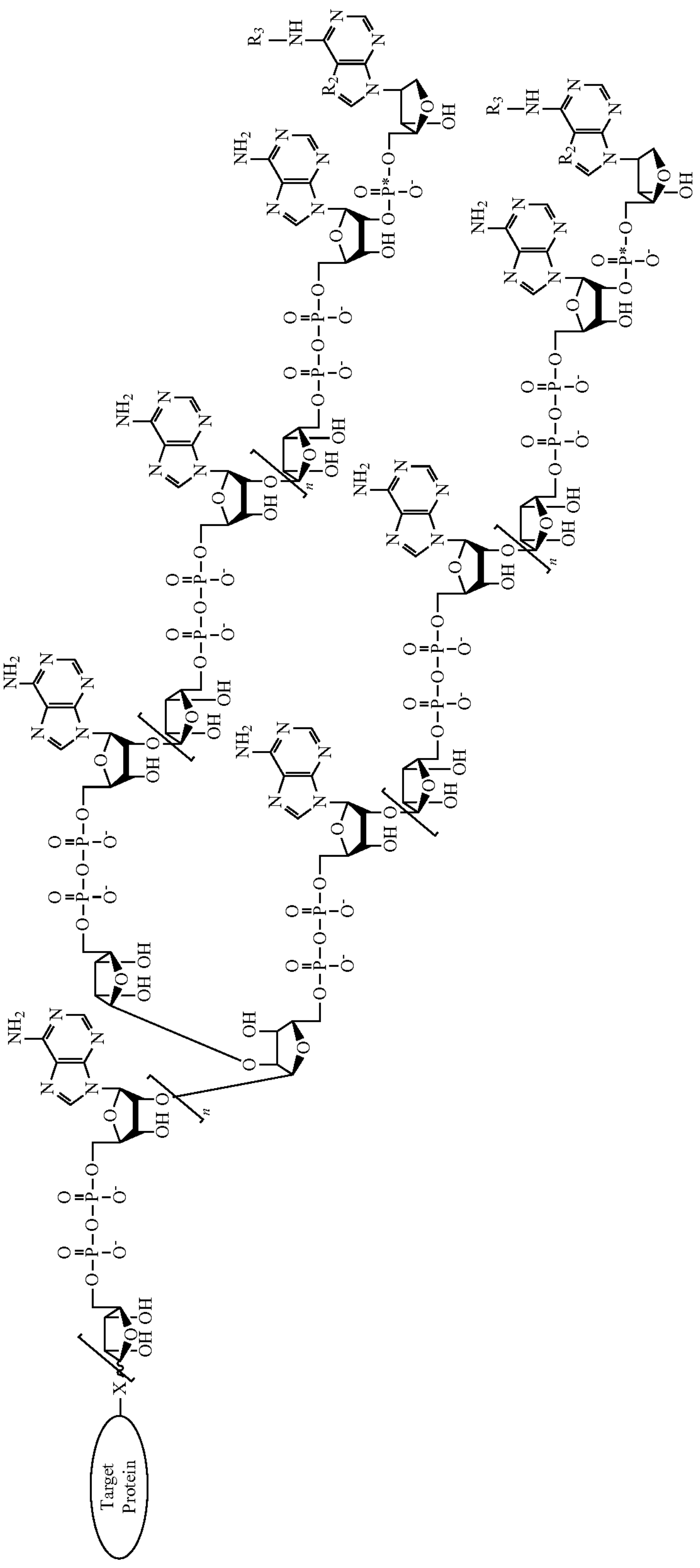
Poly(ADP-ribosyl)ated protein (with branched chain)

wherein X is O (Asp, Glu, Ser), N (Lys, Arg, Asn, Dph), or S (Cys), R2 is N, a Cy3 moiety, a Cy5 moiety; and R3 is H, a Cy5, a Biotin, or an Azido moiety; and where P* is P or $^{32}P$. The methods of the present invention may produce a protein attached to the monomer or polymer of ADP-ribose labeled at the 2'OH terminus having the structure of Formula VI:

Target Protein-ADP-ribose/PAR-X (VI)

wherein X is a label of Formula VII.

(VII)

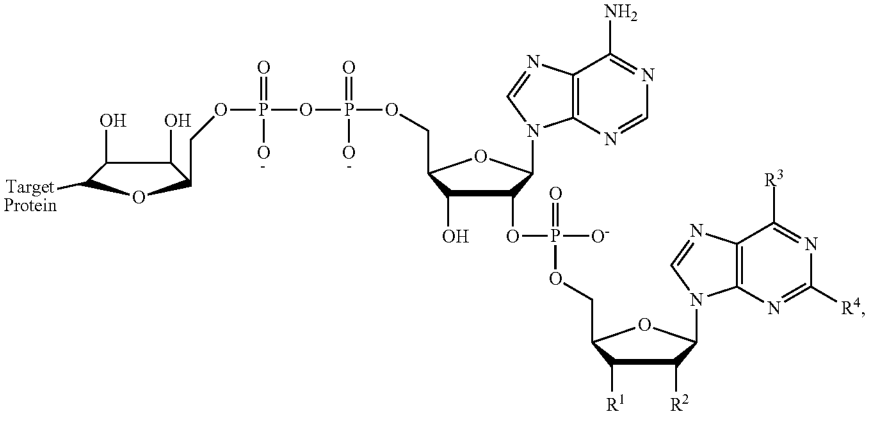

wherein $R^1$ is OH or any group selected from the following:

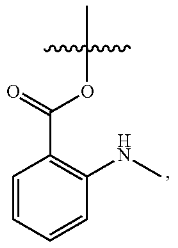

mant-

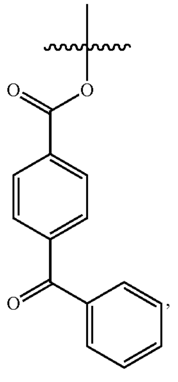

$BZ_2$-

-continued

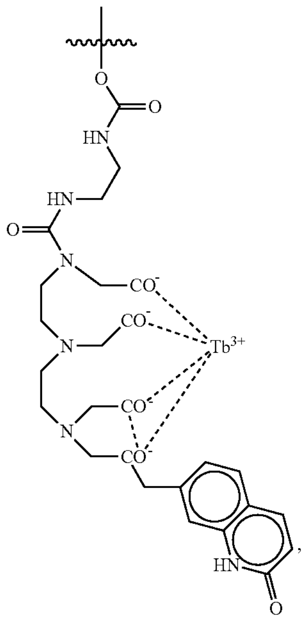

Tb-chelate-EDA-

-continued
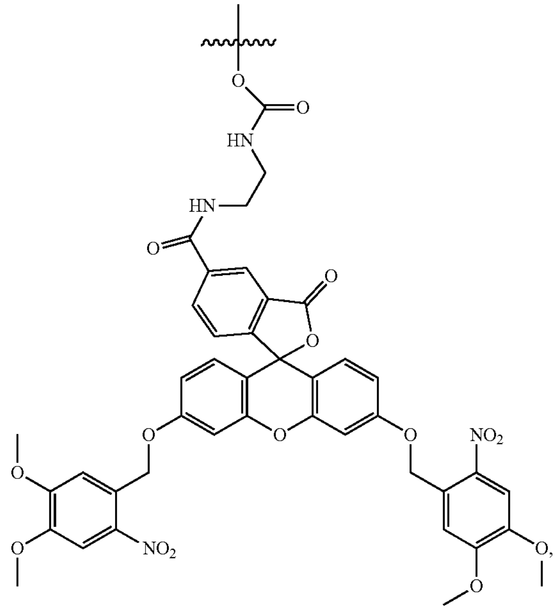
Caged FEDA-
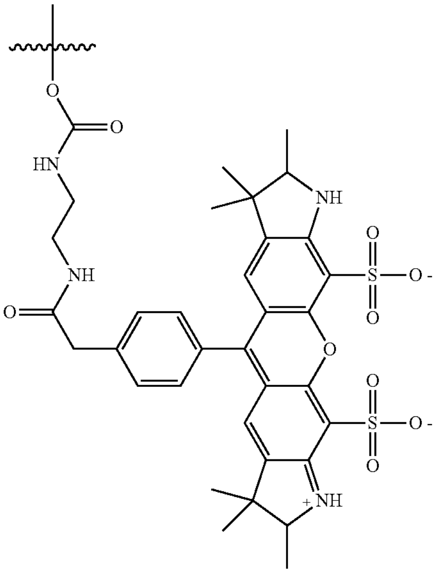
Alex$^{532}$-EDA-
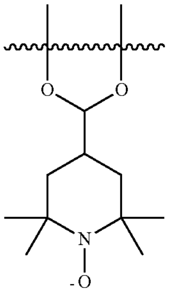
, or
2′,3′-TEMPO-
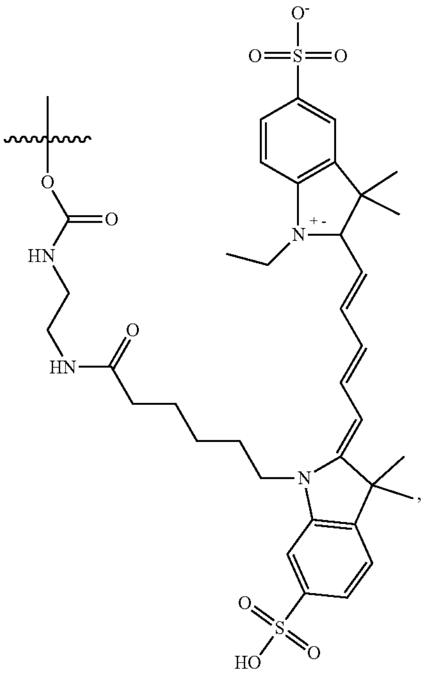
Cy5-EDA-
$R^2$ is H or OH or any group selected from the following:
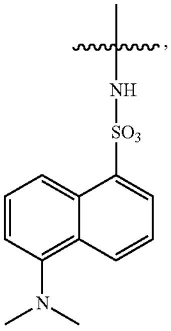
, or
2′-DNS-
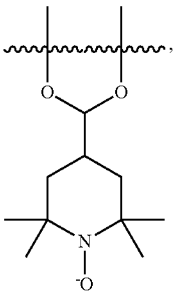
,
2′,3′-TEMPO- $R^3$ is $NH_2$ or any group selected from the following:

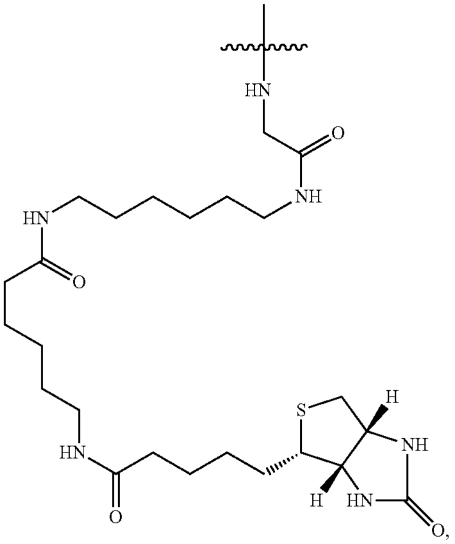

Biotin-17-

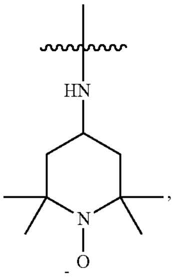

or

TEMPO-N6-

-continued

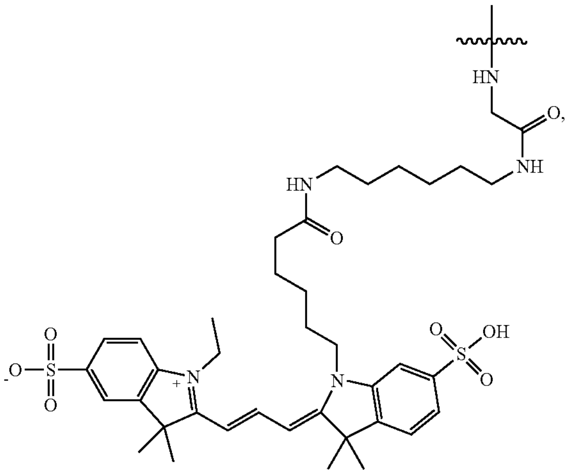

Cy3-N6- and $R^4$ is F (2-F-) or Cl (2-Cl-). Example labels include a fluorescent probe, a luminescent probe, a photoactivatable probe, a photoaffinity probe, an electron-paramagnetic-resonance (EPR) probe, an electron microscopy/enrichable probe, and a nuclear magnetic resonance (NMR) probe.

Suitable proteins used in the present invention include ADP-ribose conjugated proteins including in vitro proteins attached to the monomer or the polymer of ADP-ribose and/or in vivo proteins attached to the monomer or the polymer of ADP-ribose monomer, as examples.

Another embodiment of the present invention is a compound of Formula II, III, or IV:

(II)
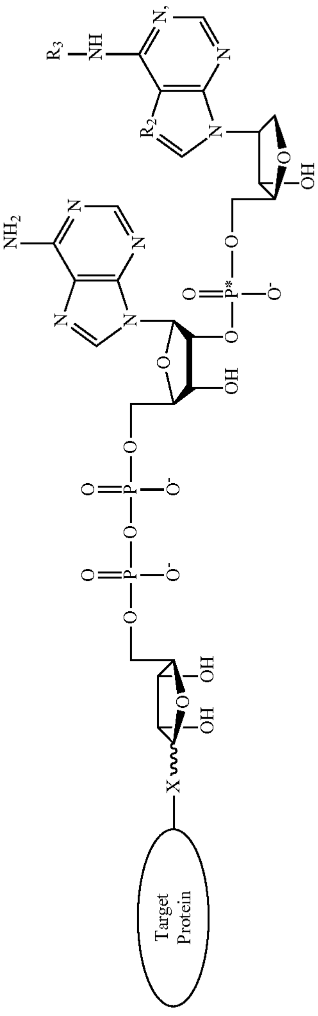
Mono(ADP-ribosyl)ated protein
(III)
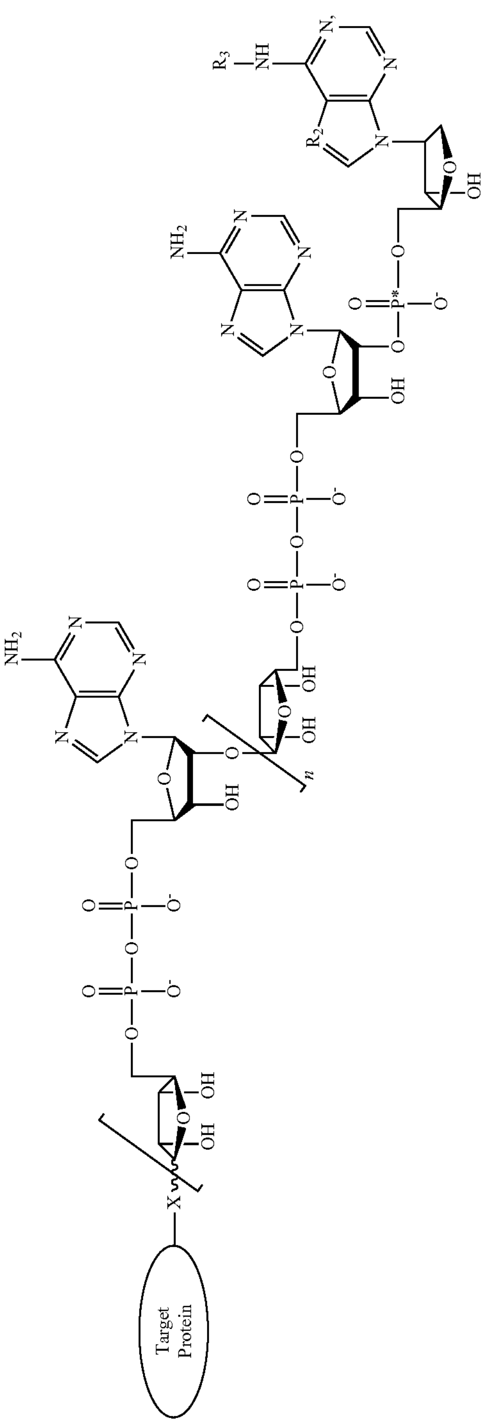
Poly(ADP-ribosyl)ated protein (with linear chain)

-continued
(IV)
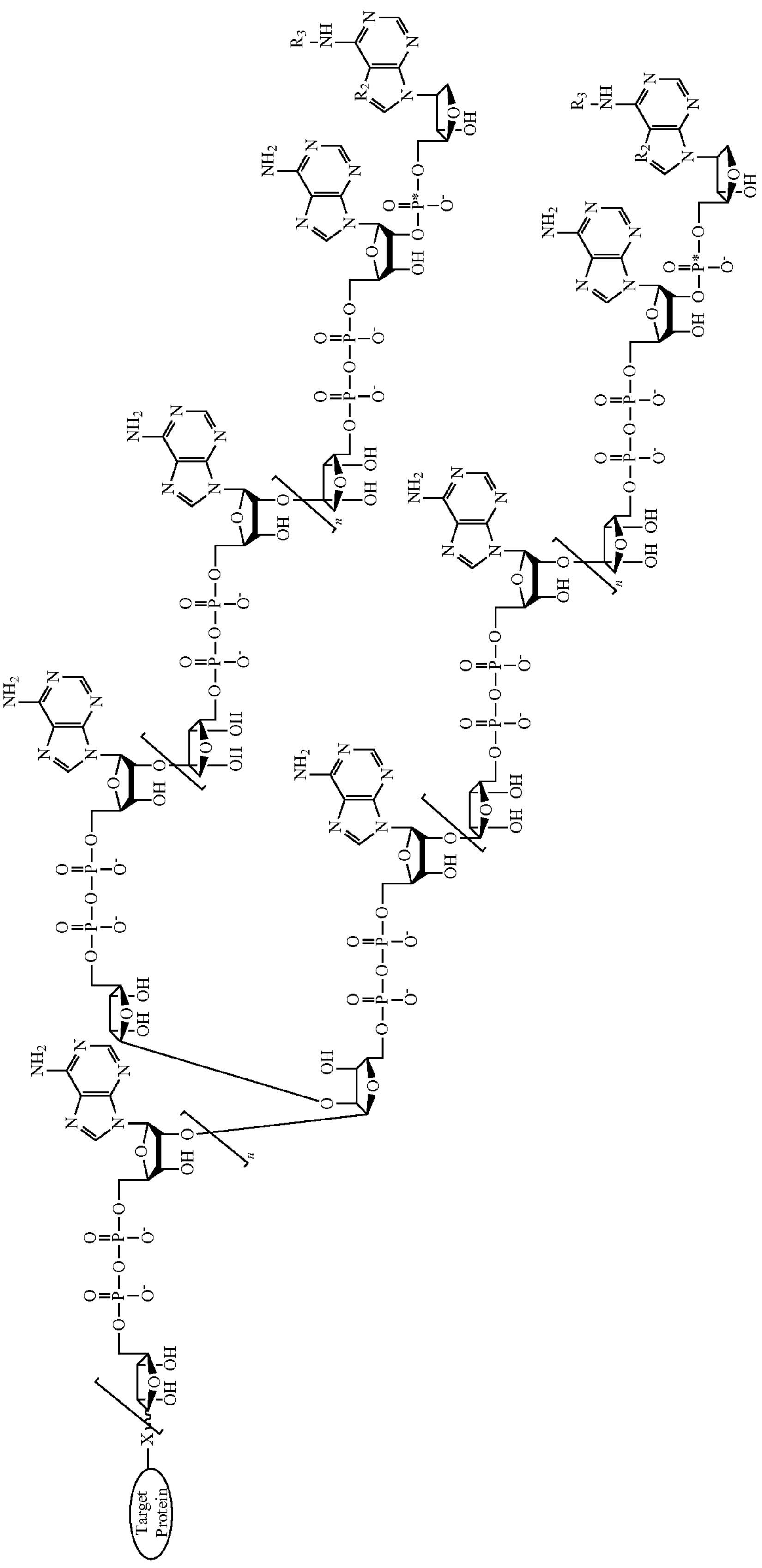
Poly(ADP-ribosyl)ated protein (with branched chain)

wherein X is O (Asp, Glu, Ser), N (Lys, Arg, Asn, Dph), or S (Cys), R2 is N, a Cy3 moiety, a Cy5 moiety; and R3 is H, a Cy5, a Biotin, or an Azido moiety; and where P* is P or $^{32}P$.

Another embodiment of the present invention is a compound of Formula (V):

ADP-ribose/PAR-X (V)

wherein X is a label of Formula VII.

Another embodiment of the present invention is a compound of Formula (VI):

Target Protein-ADP-ribose/PAR-X (VI)

wherein X is a label of Formula VII.

Another embodiment of the present invention is a method of identifying a protein ADP-ribose conjugation site. The method comprises the steps of: providing a protein/peptide attached to a monomer or polymer of ADP-ribose; incubating the cellular proteins or the digested peptide with an enzyme that attaches a label at the 2'OH terminus of the monomer or polymer of ADP-ribose wherein the label binds to a separation agent; forming a labeled protein/peptide; binding the labeled protein/peptide to a separation agent or solid support; purifying the labeled protein/peptide; identifying a protein ADP-ribose conjugation site on the labeled protein/peptide. An example is to use the label of azido-labeled dATP ($N^6$-(N-azido)hexyl-dATP) to modify ADP-ribosylated protein/peptide. The labeled protein/peptide is conjugated to solid support such as Dibenzocyclooctyne (DBCO)-agarose through ring-strain promoted copper-free click chemistry, followed by subsequent pulldown, and treatment of agarose-conjugated peptides with phosphodiesterase such as NudT16 to release protein peptides, now possessing a phosphoribose tag at former site of ADP-ribosylation, for downstream mass spectrometry analysis.

Another embodiment of the present invention are methods of labeling a polymer comprising the steps of: providing a polymer comprising an ADP-ribose; incubating the polymer with an enzyme and a label; and forming a polymer comprising an ADP-ribose labeled at the 2'OH terminus. Examples of suitable polymer include a nucleic acid, a protein, a peptide, a polymer of ADP-ribose, and a combination thereof. Suitable nucleic acids include DNA or RNA, that maybe double or single-stranded and that maybe PARylated or MARylated. Suitable proteins or peptides include enzymes, or functional parts thereof, and antibodies, or functional parts thereof, as examples. The proteins or peptides may be PARylated or MARylated.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The term "activity" refers to the ability of a gene to perform its function.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "disease" is meant any condition, disorder that damage, or interferes with the normal function of a cell, tissue, or organ.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "express" refers to the ability of a gene to express the gene product including for example its corresponding mRNA or protein sequence (s).

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

"MARylated" means when ADP-ribosylation results in the transfer of a single mono(ADP-ribose) (MAR) group on a protein or nucleic acid.

"PARylated" means when ADP-ribosylation results in the transfer of multiple ADP-ribose (ADPr) group on a protein or nucleic acid.

"ADP-ribosylation" including both "MARylation" and "PARylation", is catalyzed by an enzyme such as ADP-ribosyltransferases including poyly(ADP-ribose)polymerase (PARPs), arginine-specific ecto-enzymes such as ARTC1-6 and a lot of bacterial toxins. Examples of ADP-ribosyltransferases include, in humans, PARPs, and in bacteria, a bacterial toxin DarT.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

By "reduces" is meant a negative alteration of at least 10%, 25%, 50%, 75%, or 100%.

A "reference" refers to a standard or control conditions such as a sample (human cells) or a subject that is a free, or substantially free, of an agent such as OAS.

As used herein, the term "sensitivity" is the percentage of subjects with a particular disease.

As used herein, the term "specificity" is the percentage of subjects correctly identified as not having a particular disease i.e., normal or healthy subjects.

As used herein, the term "subject" is intended to refer to any individual or patient to which the method described herein is performed. Generally, the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

DETAILED DESCRIPTION OF THE INVENTION

ADP-ribosylation—the addition of one or more ADP-ribose groups onto proteins—is a therapeutically important but understudied protein modification. The attached ADP-ribose monomer or polymer, commonly known as poly (ADP-ribose) (PAR), modulate the activities of the modified substrates and/or their binding affinity to other proteins. However, there is a lack of tools to investigate this protein modification or PAR as a polynucleotide. Here, the inventors describe ELTA (Enzymatic Labeling of Terminal ADP-ribose) for the labeling of free, protein-conjugated, or nucleic acid-conjugated ADP-ribose monomer and polymers at the 2'-OH terminus. When coupled with a diverse range of chemical tags (e.g., radioactive, fluorescent, biotin-tag, clickable functional groups), ELTA can be used to adapt techniques routinely used to investigate DNA or RNA functions to explore PAR biology. Here the inventors demonstrate that ELTA enables the quantitative measurement of PAR binding to proteins in vitro, detection of endogenous PAR from cells and enrichment of ADP-ribosylated peptides from complex samples.

Figure 1A:
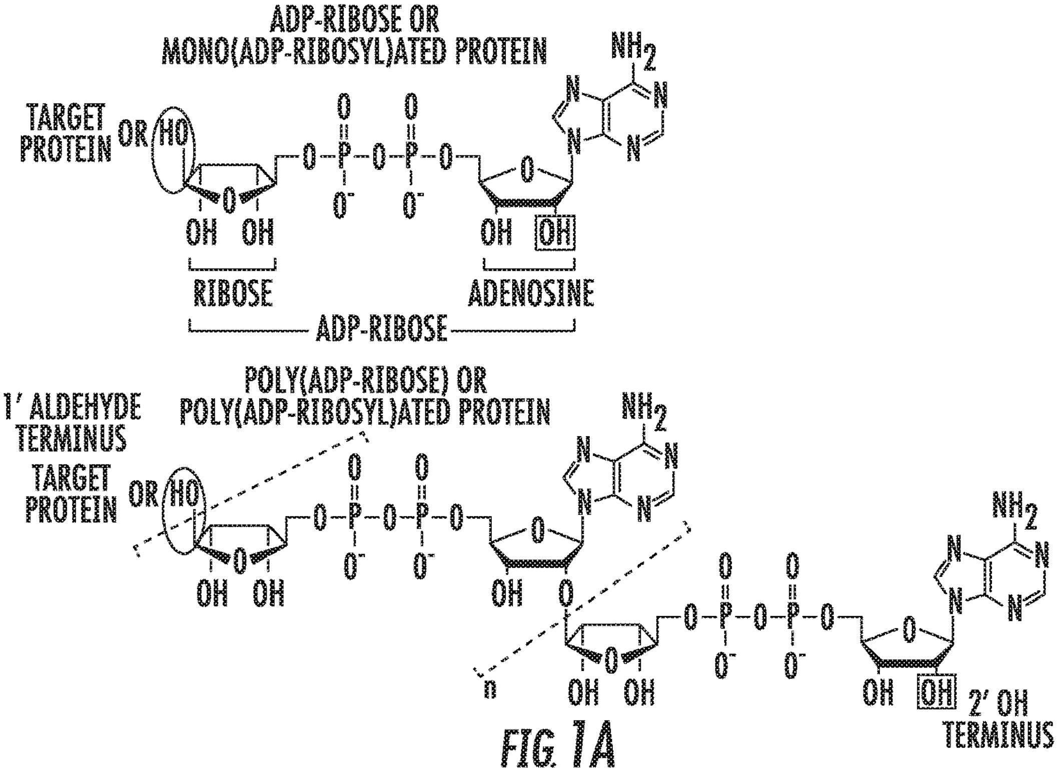
FIG. 1A-1F illustrates (a) the general scheme of free and protein-conjugated ADP-ribose monomer and polymer, where the 2'OH terminus is indicated in green. (b) The addition of dAMP group onto ADP-ribose and $NAD^+$, but not iso-ADP-ribose upon incubation with OAS1, poly(I:C) and dATP. (c) Matrix-Assisted Laser Desorption/Ionization Time-of-Flight (MALDI-TOF) Mass Spectrometry analysis of the reaction before and after the incubation of ADP-ribose, dATP, poly(I:C) and OAS1 (d) The addition of dAMP group onto ADP-ribose and poly(ADP-ribose) of different length. (e) The addition of dAMP group onto the catalytic domain of poly(ADP-ribose) polymerase 10 ($PARP10^{CD}$) as an example for protein-conjugated ADP-ribose monomer or mono(ADP-ribosyl)ated proteins. (f) The addition of dAMP group onto *Herpetosiphon aurantiacus* PARP (haPARP) as an example for protein-conjugated ADP-ribose polymer or poly(ADP-ribosyl)ated proteins

The Basis of ELTA: OAS1 Adds dATP onto 2'-OH Termini of ADP-Ribose Monomers and Polymers To label ADP-ribose and its derivatives at the 2'-OH terminus (FIG. 1*a*, green), the inventors propose to use the enzyme 2'-5'-Oligoadenylate Synthetase 1 (OAS1). OAS1 is activated by double-stranded RNAs and oligomerizes ATP into 2'-5' linked oligoadenylate, where the α-phosphate of the donor ATP is linked to the 2'-OH of the acceptor ATP, resulting in the addition of an AMP moiety onto the acceptor ATP in a 2'-5' linkage. Previous data suggested that OAS1 may have the potential to be used as a labeling tool. First, OAS1 has been shown to link donor ATP not only to an acceptor ATP, but also onto 2'-OH of molecules that contain adenosine as acceptors, including $NAD^+$[20,21] and ADP-ribose[22]. Second, OAS1 can use other NTPs such as deoxy-ATP (dATP) as donors. We reasoned that the lack of 2'-OH group in dATP results in chain termination and, therefore, dATP would be an ideal donor substrate of OAS1 to end-label the 2'-OH terminus of free and protein-conjugated ADP-ribose monomers or polymers. However, it is unclear whether dATP can be added onto these acceptor molecules.

Figure 1B:
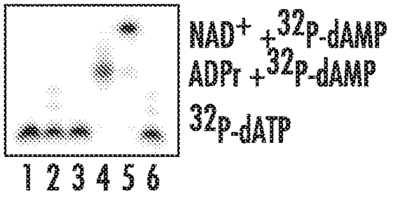
Figure 1C:
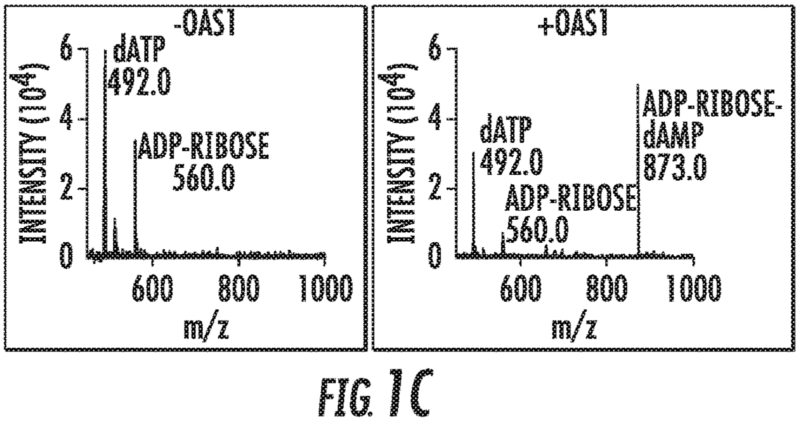
Figure 2A:
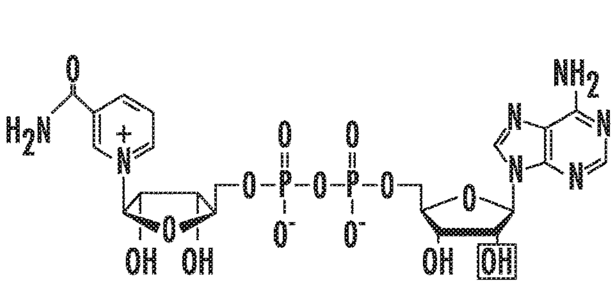
FIG. 2A-2C illustrates (a) the structure of $NAD^+$ and iso-ADP-ribose; (b) the separation of individual PAR chain length by high performance liquid chromatography (HPLC); (c) the SYBR GOLD staining of 6 mer, 10 mer, 15 mer, 21 mer and 25 mer of PAR (left); the labeling of these individual chain length by ELTA using $^{32}$P-dATP (right); the quantitation of the signal of radioactivity (bottom).
Figure 2A:
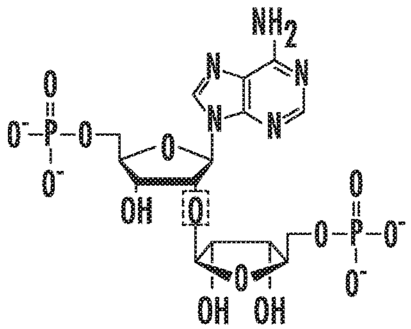

To test whether OAS1 can add dATP onto ADP-ribose (ADPr) in vitro, recombinant OAS1 was incubated with α-$^{32}$P-dATP and ADPr (FIG. 1*b*). As expected, a major product running at the molecular weight of dAMP+ADPr was observed. As expected, dAMP can be added onto 2'-OH group of $NAD^+$; however, the internal unit of PAR, iso-ADP-ribose, which does not have a free 2'-OH in the adenosine-linked ribose, cannot be served as an acceptor even though a similar concentration was used (as indicated by A260 value; FIGS. 1*b* and 2*a*). To further confirm the addition of dAMP moiety onto ADP-ribose by OAS1, MALDI-TOF analyses were performed (FIG. 1*c*). In the absence of OAS1, dATP and ADP-ribose were observed at m/z of 492.0 and 560.0, respectively. In the presence of OAS1, an additional peak was observed at m/z of 873.0, which corresponds to the expected molecular weight of ADP-ribose-dAMP.

Figure 1D:
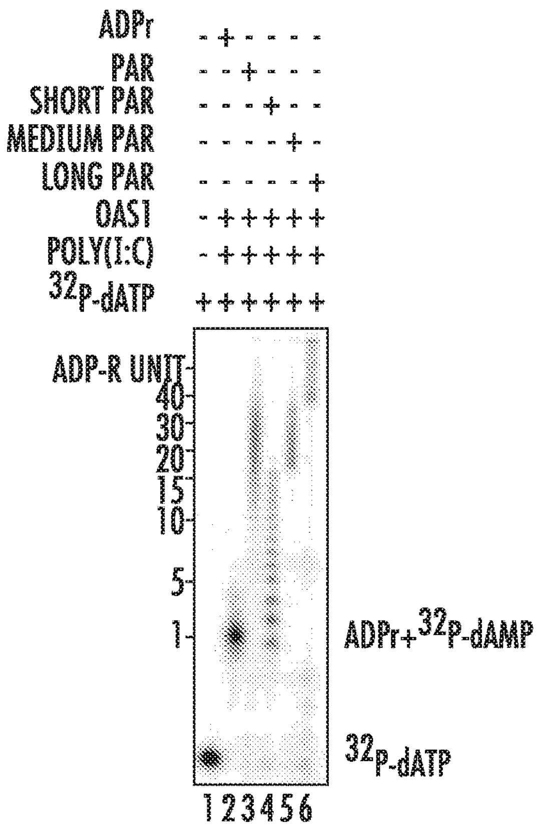
Figure 2B:
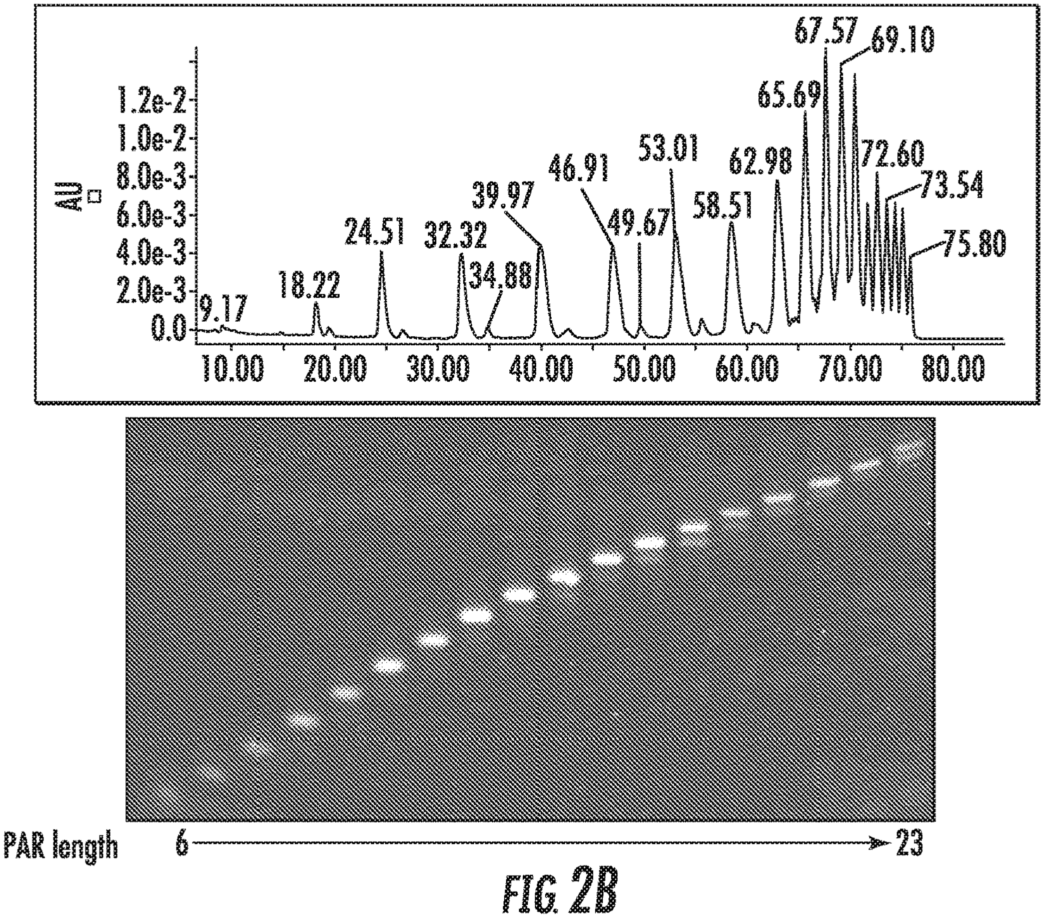
Figure 2C:
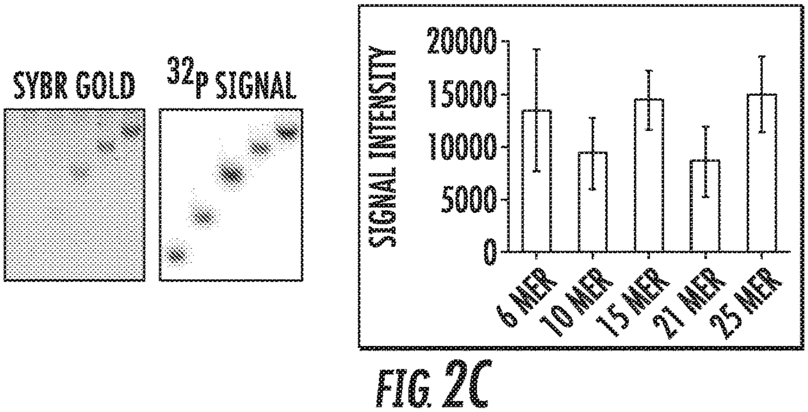

Given that the internal unit of PAR cannot be labeled (FIG. 1*b*) but each linear PAR chain has one 2'-OH terminus (cf. FIG. 1*a*), we next investigated whether PAR can also be end-labeled by incubating OAS1 and $^{32}$P-dATP with different chain lengths of ADP-riboseshort (≤15 mers), medium (15-40 mers) and long (≥40 mers) (FIG. 1*d*). In each case, these PAR molecules of different lengths were effectively labeled. To test whether this OAS method can label PAR chain of different length with comparable efficiency, we optimized a purification method to efficiently separate PAR to defined chain length (FIG. 2*b*). The inventors then used the same $^{32}$P-dATP-OAS1 method to label the defined length PAR chains. As expected, these PAR chains of different length were labeled with comparable efficiency (FIG. 2*c*). Taken together, OAS1 can label both ADP-ribose monomer and polymers at their 2'-OH termini using radio-labeled dATP.

OAS1 Adds dATP Analogs onto Protein-Conjugated ADP-Ribose

Figure 1E:
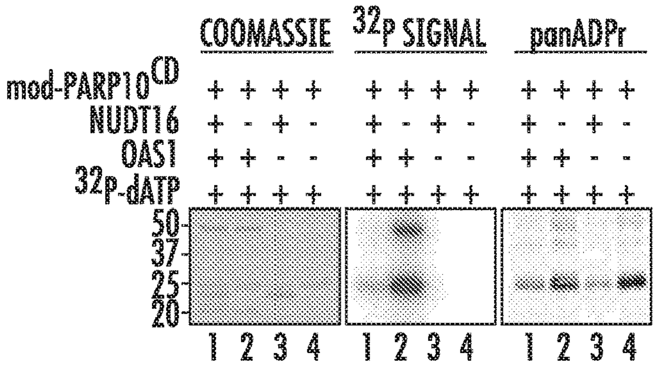
Figure 1F:
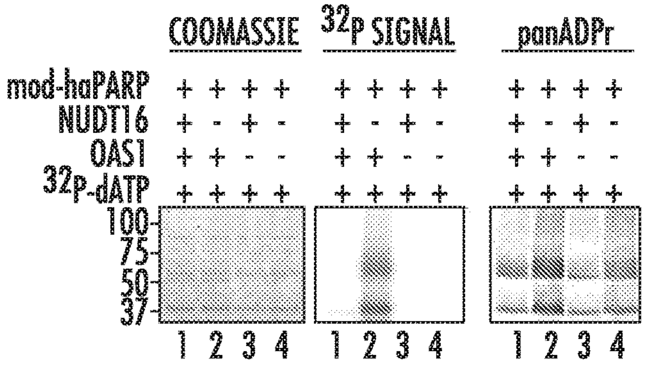

As ADP-ribose can be conjugated to protein at the 1" terminus, the inventors reasoned that the free 2'-OH group of protein-conjugated ADP-ribose could also be served as substrates of OAS1. Using automodified PARP-10 catalytic domain ($PARP10^{CD}$) or haPARP as model substrates for mono(ADP-ribosyl)ated (MARylated) and poly(ADP-ribosyl)ated (PARylated) substrates, respectively, the inventors tested whether these ADP-ribosylated substrates can be labeled by OAS1 with $^{32}$P-dATP (FIG. 1*e, f*). As a negative control, we pre-treated the ADP-ribosylated substrates with hsNudT16, which cleaves the pyrophosphate bond within ADP-ribose (cf. FIG. 1*a*) to leave a phosphoribose tag on previously ADP-ribosylated proteins. As a result, the 2'-OH containing adenosine is removed and these phosphoribosylated proteins are no longer recognized by Af1521 macrodomain (pan-ADPr reagent[27]) nor OAS1 for labeling. On the contrary, MARylated $PARP10^{CD}$ and PARylated haPARP were labeled by $^{32}$P-dATP in the presence of OAS1, and such signals were quantitatively reduced in the sample pre-treated with hsNudT16 (FIG. 1*e, f*). Therefore, this OAS1-based method enables the inventors to effectively label both protein-conjugated ADP-ribose monomer and polymers.

Figure 3A:
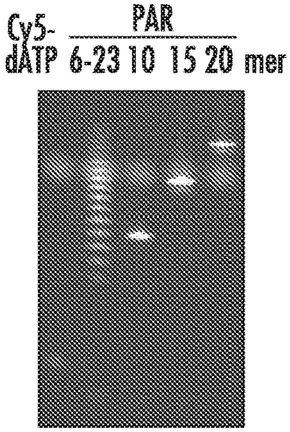
FIG. 3A-3D illustrates (a) the labeling of a mixture of 6-23 mers, 10 mer, 15 mer, 20 mer PAR by ELTA with Cy5-dATP. (b) An example of labels that can be used with the ELTA labeling method, including radioactive, fluorescent, biotin, and clickable variations that can be modified at different positions of the dATP molecule. (c-d) An example of using ELTA-modified ADP-ribose for biophysical measurement: (c) Filter binding assay of RNF146 WWE domain binding to 10 mer and 20 mer PAR, which was radiolabeled using ELTA method. (d) Microscale Thermophoresis analysis of RNF146 WWE doming binding to 20 mer PAR, which was labeled using ELTA and Cy5-dATP.
Figure 3B:
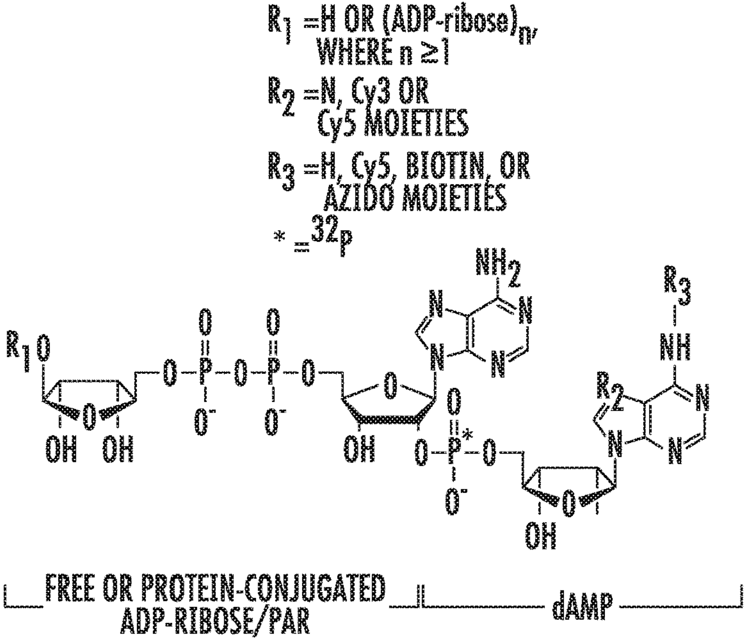
Figure 4A:
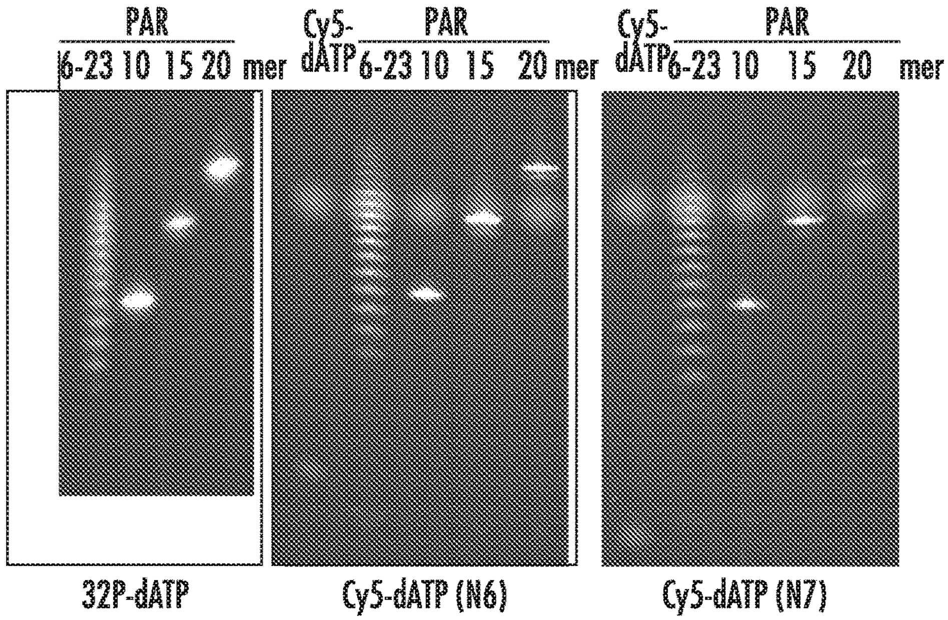
FIG. 4A-4C illustrates (a) the labeling of a mixture of 6-23 mers, 10 mer, 15 mer, 20 mer by ELTA with $^{32}$P-dATP, Cy5-dATP modified at N6 position, Cy5-dATP modified at N7 position. (b) the labeling of PAR with Cy3-dATP by ELTA. (c) the labeling of PAR with biotin-dATP by ELTA.
Figure 4B:
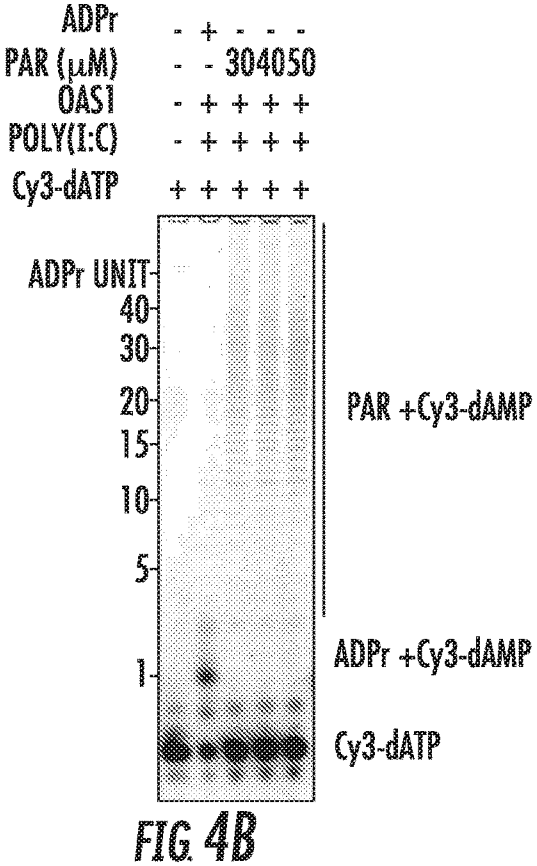
Figure 4C:
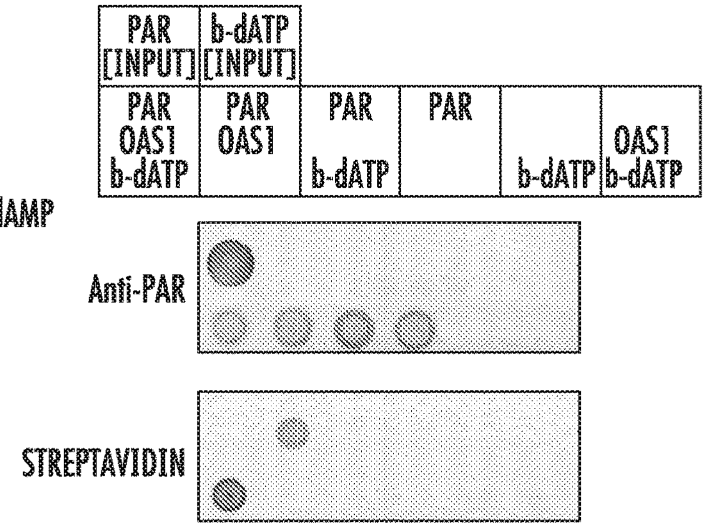
Figure 5A:
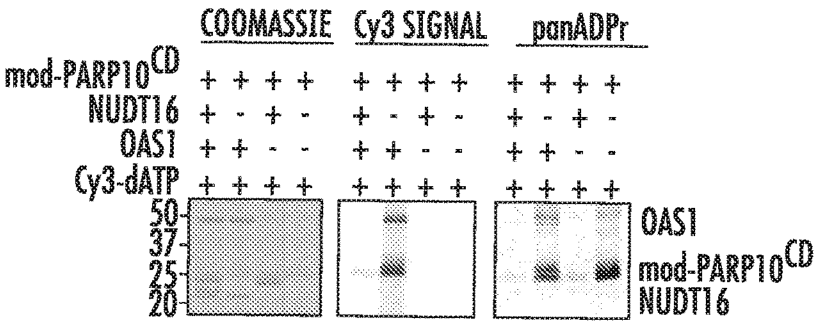
FIG. 5A-5E illustrates (a) the addition of dAMP group onto $PARP10^{CD}$ as an example for mono(ADP-ribosyl)ated proteins using ELTA with dATP conjugated at the 7 position with Cy3 (Cy3-dATP). (b-c) the addition of dAMP group onto $PARP10^{CD}$ (panel b) as an example for mono(ADP-ribosyl)ated proteins using ELTA with Biotin-14-dATP, a dATP analog with biotin attached at the 6-position of the purine base by a 14-atom linker, using non-ADP-ribosylated protein Bovine Serum Albumin (BSA) as a negative control (panel c). (d) ELTA reaction for labeling $PARP10^{CD}$ using $^{32}$P-dATP with or without 1M denaturant urea. (e) ELTA reaction for labeling ADP-ribose using $^{32}$P-dATP under a range of denaturing and detergent conditions.
Figure 5B:
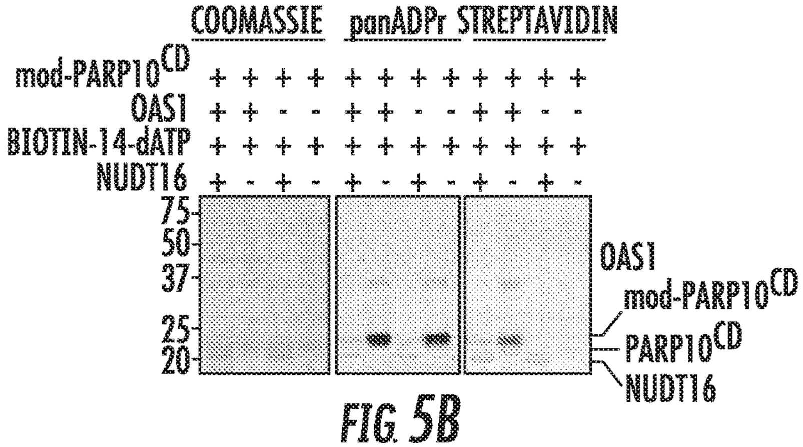
Figure 5C:
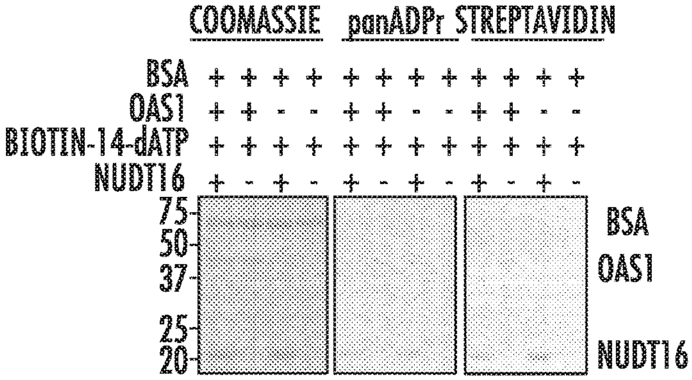
Figure 5D:
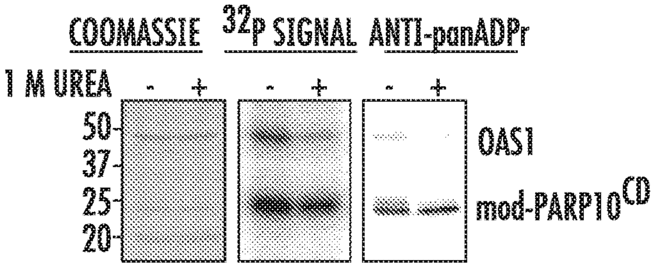
Figure 5E:
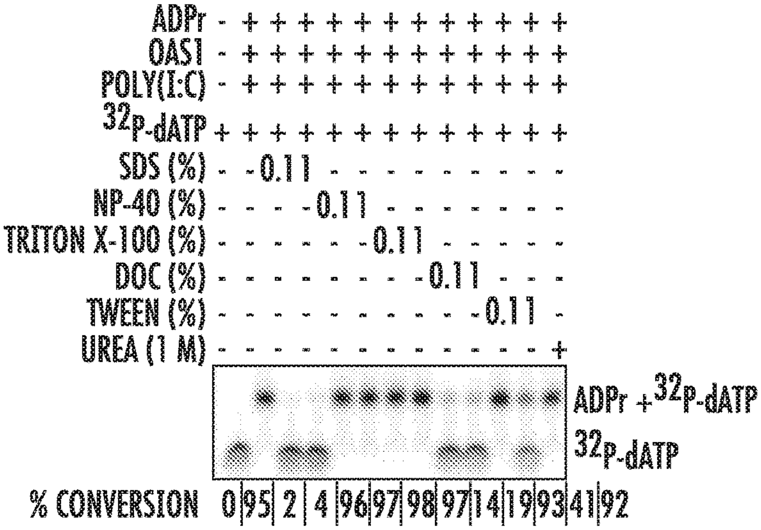

OAS1 is a Versatile Enzyme that Accepts Different Modified dATP Analogs for Labeling Next, the inventors investigated whether the OAS1 enzymatic labeling reaction can be extended to the labeling of ADP-ribose with modified dATP analogues (e.g., fluorescent, biotin-tag, clickable functional groups). Following a similar labeling protocol, we used Cy5-dATP attached at two different positions on the adenine base (6' and 7'; FIGS. 3*a,b* and 4*a*). The inventors were able to efficiently label 3 different PAR chains lengths (10 mer, 15 mer, and 20 mer) and a mixture of 6-23 mer PAR chains with the two Cy5 labels (FIG. 4*a*). OAS1 labeling can also be performed with other fluorescent derivatives such as Cy3 (FIG. 4*b*) and a biotinylated dATP modified on the 6' position via a 14-carbon linker (FIG. 4*c*). Similarly, this labeling reaction can also be performed on protein-conjugated ADP-ribose using modified dATP as well as performed in a range of detergent and denaturant conditions (FIG. 5).

Given the versatility of OAS1 to label free and protein-conjugated ADP-ribose using a range of modified dATP analogues, the inventors named this general method to enzymatically label terminal ADP-ribose as ELTA. Using several proof-of-concept applications, the inventors will illustrate below how to use ELTA for measurement, detection and enrichment in ADP-ribosylation biology.

Figure 3C:
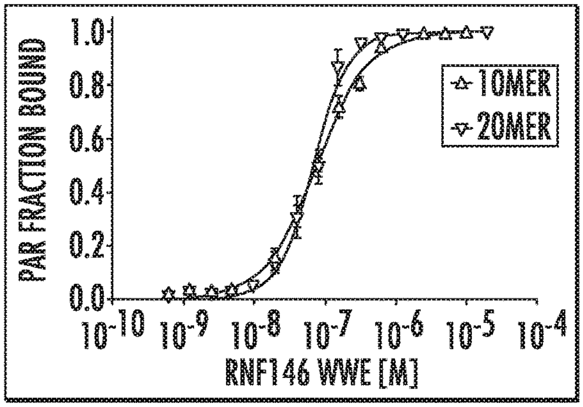
Figure 3D:
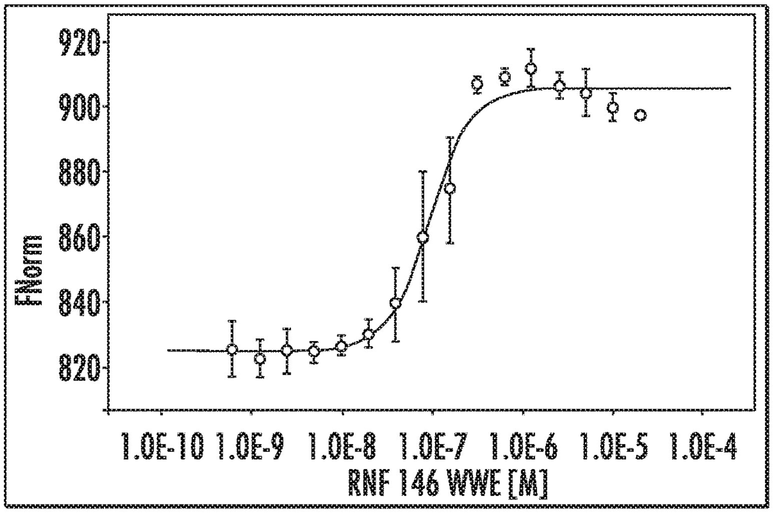

Labeled PAR Chain Can be Used to Measure the Affinity of PAR Binding to Protein In Vitro Poly(ADP-ribosyl)ation (PARylation) of target proteins regulates many biological processes. For example, PAR recognition by WWE domain of RNF146 is required for the poly-ubiquitination and subsequent degradation of axin—a key regulator of Wnt signaling pathway. PAR-protein binding affinity measurement for RNF146 WWE has been evaluated either with a mixed population of PAR or with the internal unit iso-ADP-ribose as a proxy using isothermal titration calorimetry (ITC), which requires a significant amount of materials (typically at μM). PAR-binding affinity has also been assayed using nanomolar amounts of fluorescently labeled PAR by fluorescent polarization, or biotinylated PAR by electrophoretic mobility shift assay or surface plasmon resonance. However, both methods require PAR synthesis and conjugation through chemical methods, which are not readily accessible to most molecular biology laboratories. Here, by combining ELTA with the inventors' improved single chain PAR purification, the inventors were able to measure the affinity of a single length PAR chain to the WWE domain of RNF146. First, the inventors used a filter-binding assay and measured the affinity of radiolabeled 10 and 20 mer PAR to RNF146 (FIG. 3*c*). Both PAR chains bind tightly to RNF146 WWE domain with affinities of 75 nM (10 mer) and 67 nM (20 mer), which are comparable with the affinity reported for the RNF146 WWE-iso-ADP-ribose binding. The inventors further extended the repertoire of biophysical measurement of the PAR binding assays by using the commonly used Cy5 fluorescence dye and measured the affinity Cy5-PAR to RNF146 using Microscale Thermophoresis (MST). The binding affinity was similar to the affinity measured using the filter binding assays (FIG. 3*d*).

ELTA Labels PAR Isolated In Vitro and from Cells for Assessing Polymer Length

Figure 6A:
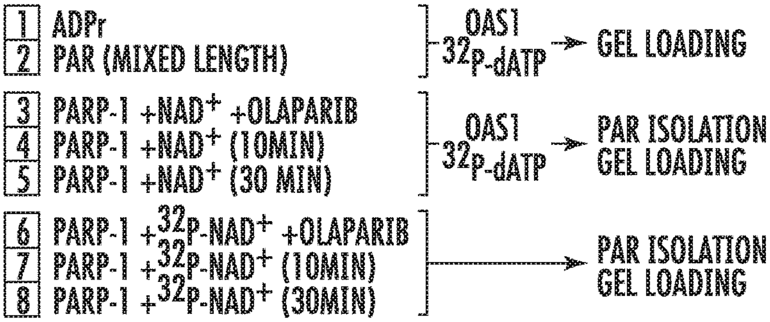
FIG. 6A-6B illustrates the detection of ADP-ribose length using ELTA. (a) A sequencing gel of the ELTA labeling reaction of ADP-ribose monomer (lane 1), PAR (lane 2), and of ADP-ribose monomer and polymer isolated from in vitro ADP-ribosylated PARP1 by $NAD^+$ in the presence of the PARP inhibitor Olaparib (lane 3), by $NAD^+$ for 10 min in the absence of Olaparib (lane 4) and by $NAD^+$ for 30 min (lane 5). As a comparison, the ADP-ribose monomer and polymer isolated from in vitro ADP-ribosylated PARP1 by NAD+ with a trace of $^{32}$P-NAD+ in the presence of Olaparib for 30 min (lane 6), by $NAD^+$ for 10 min in the absence of Olaparib (lane 7) and by $NAD^+$ for 30 min (lane 8). (b) A sequencing gel of the ELTA labeling reaction of ADP-ribose monomer and polymer isolated from in vitro ADP-ribosylated haPARP (lane 1), from untreated cancer cells (lane 2), from cancer cells with DNA damage (lane 3), from cancer cells with DNA damage and treated with PARP inhibitor (lane 4) and from cancer cells with DNA damage and treated with PARG inhibitor (lane 5).
Figure 6A:
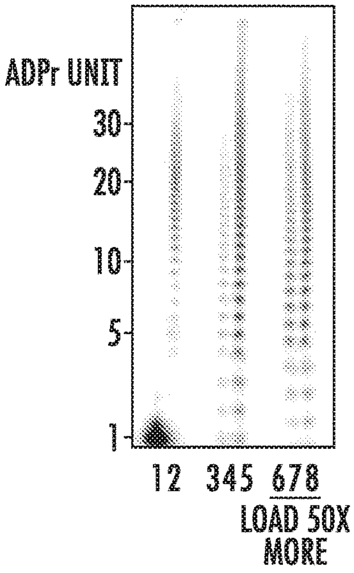

The number of ADP-ribose units attached to proteins is dynamically regulated within cells and notably, protein binding to PAR is dependent on the length of PAR chain. However, it is not possible to examine the length of PAR from modified substrates without prior labeling (e.g., using radioactive $NAD^+$). Given that ELTA can effectively label pre-made PAR, the inventors tested whether this labeling technique can be used to assess the chain length of PAR isolated from modified substrates and compared with the existing technique that requires prior labeling. To examine the labeling efficiency of PAR isolated from PARylated PARP1, the inventors modified PARP1 with 1 mM $NAD^+$ with or without a trace of $^{32}P\text{-}NAD^+$ for either 0, 10, 30 min. PAR was extracted from both non-radioactive and radioactive samples. The non-radioactive samples were further labeled with OAS1 and $^{32}$P-dATP. All samples were then run on a 15% denaturing urea gel for autoradiography. As shown in FIG. 6*a*, the patterns of isolated PAR sample labeled by $^{32}P\text{-}NAD^+$ and $^{32}$P-dATP are comparable in length distribution. However, the inventors note that ELTA is more sensitive: though the $^{32}$P-dATP and $^{32}P\text{-}NAD^+$ labeled PAR appear similar in intensity, the inventors loaded 50-fold less PAR in lanes 3, 4 and 5. Therefore, ELTA provides a sensitive approach to assess the polymer length of a PARylated protein without prior labeling.

Figure 6B:
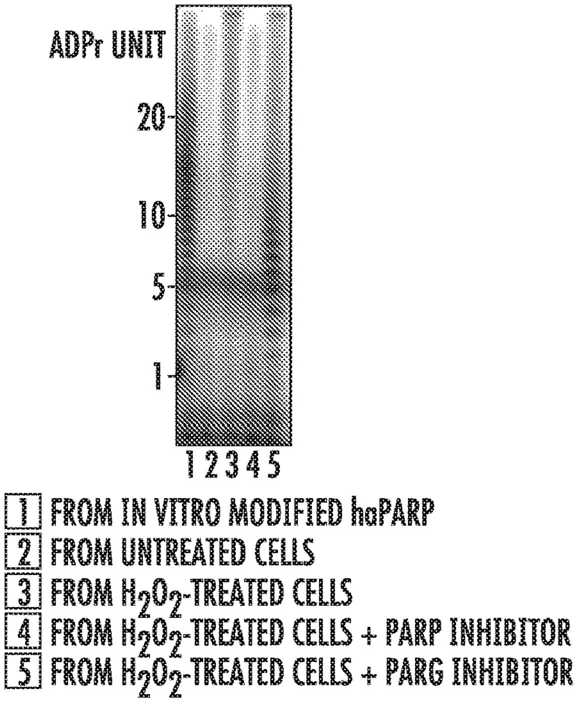

Next, the inventors tested whether ELTA can be used to examine PAR isolated from cells (FIG. 6*b*). PAR was retrieved from cells using a solid-phase extraction method that allows for the high recovery of PAR without any bias of different chain length. HaCaT cells were either untreated, $H_2O_2$-treated to induce PARylation, pre-treated with PARP inhibitor Olaparib prior to $H_2O_2$ induction of PAR, or pre-treated with inhibitor against the PAR-degrading enzyme PARG (PDD 00017273) prior to $H_2O_2$ induction of PAR. As a control, the inventors also isolated PAR from in vitro modified *Herpetosiphon aurantiacus* PARP (haPARP), which usually generates PAR of 2-25 mer (lane 1), using the same solid-phase extraction method. As expected, we observed significant PAR signals in $H_2O_2$-treated cell samples (FIG. 6*b*; lane 3), which is longer from the one isolated from haPARP (lane 1). PARP inhibitor Olaparib (lane 4) reduced the signal to background level as in the untreated cells (lane 2). On the contrary, PARG inhibitor resulted in the enrichment of overall signals and, intriguingly, stronger signals were observed at a shorter range at the tested conditions (lane 5). Taken together, ELTA can assess the length of PAR isolated in vitro or from cells.

ELTA Allows for Selective Labeling and Enrichment of ADP-Ribosylated Peptides

Building on our findings that ELTA can be used to label protein-conjugated ADP-ribose (c.f. FIG. 1*e, f*); we sought to develop a workflow for selective labeling and enrichment of ADP-ribosylated peptides from cell lysates for downstream proteomic analysis. The inventors propose a pipeline composed of three steps (FIG. 7*a*): 1) the labeling of ADP-ribosylated peptides with the "clickable" dATP analogue, $N^6$-(N-azido)hexyl-dATP, by OAS1, 2) conjugation of OAS1-labeled peptides to Dibenzocyclooctyne (DBCO)-agarose through ring-strain promoted copper-free click chemistry, followed by subsequent pulldown, and 3) treatment of agarose-conjugated peptides with hsNudT16 phosphodiesterase to release peptides, now possessing a phosphoribose tag at former site of ADP-ribosylation, for downstream analysis.

Figure 7A:
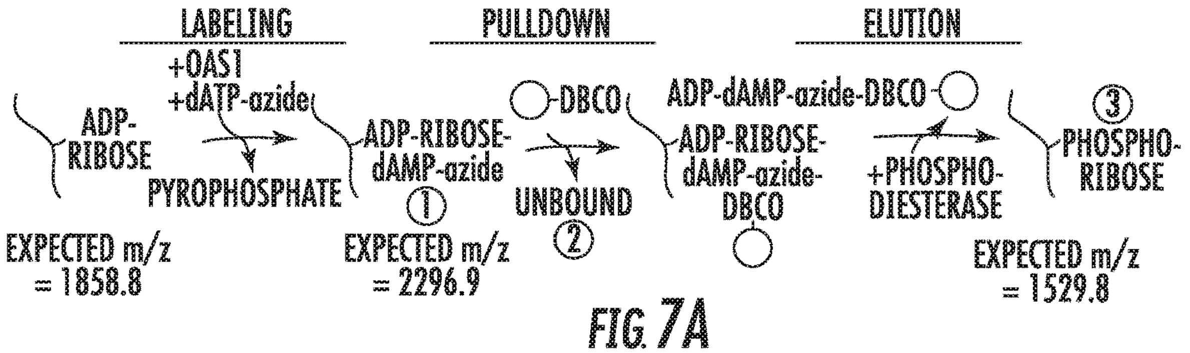
FIG. 7A-7E illustrates an example for the use of ELTA to enrich ADP-ribosylated substrates. (a) the schematics of the pipeline. Panel (b) demonstrates the m/z ratio of peptide (1) after ELTA labeling reaction, (2) in the unbound fraction from the solid support, (3) after elution with phosphodieaterse. Red lines indicate samples with OAS1 and black lines indicate samples without OAS1. (c) The total intensity chromatograph (TIC) of the lysate input sample (left) and of the enriched sample after elution (middle) and the mass spectrometry scan analyses at retention time of 6.36 minutes. (d) Tandem Mass spectrometry (MS/MS) spectra of ADP-ribosylated peptide with the modification site signified by the addition of a phosphoribose group and (e) Quantification of peptide-spectrum match (PSM) of the nanomole, picomole and femtomole of ADP-ribosyalted peptide dosed in milligram of cell lysate peptides.
Figure 7B:
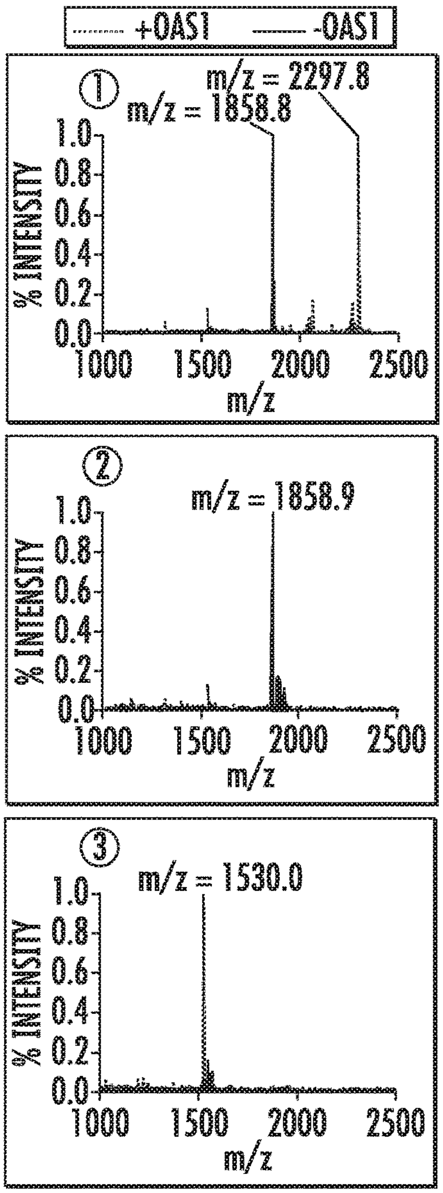

First, the inventors tested whether OAS1 can label an ADP-ribosylated peptide, HK533, with $N^6$-(N-azido)hexyl-dATP and analyzed the reaction product by MALDI-TOF. As expected, a peak shift of 438.9 Da was observed (FIG. 7*b*, panel 1), which corresponds to $N^6$-(N-azido)hexyl-dAMP. Next, we incubated this reaction with DBCO-agarose to allow for the conjugation of OAS1-labeled HK533 to the resin. The inventors observed that there are no peaks in the mass range of OAS1-labeled HK533 in the unbound fraction, suggesting that a large proportion of the OAS1-labeled HK533 was conjugated to and pulled down by the DBCO-agarose (FIG. 7*b*, panel 2). Consistently, the unlabeled HK533 peptide were present in the unbound fraction of the sample not treated with OAS1, but absent in the OAS1-treated samples. These data indicate that unlabeled HK533 is not significantly retained by the DBCO-agarose (FIG. 7*b*, panel 2). To confirm the conjugation of OAS1-labeled HK533 peptide with the resin, the inventors treated the peptide-conjugated DBCO-agarose resin with hsNudT16 phosphodiesterase (cf. FIG. 1*e, f*; FIG. 7*a*). The inventors observed a defined peak at the expected m/z for phosphoribosylated HK533 (observed m/z 1530.0; expected m/z 1529.8) in the eluent of the peptide sample treated with OAS1 and no significant peaks in the sample without OAS1 (FIG. 7*b*, panel 3). Together these results demonstrate the feasibility of this workflow for the labeling and enrichment of ADP-ribosylated peptides.

Figure 7C:
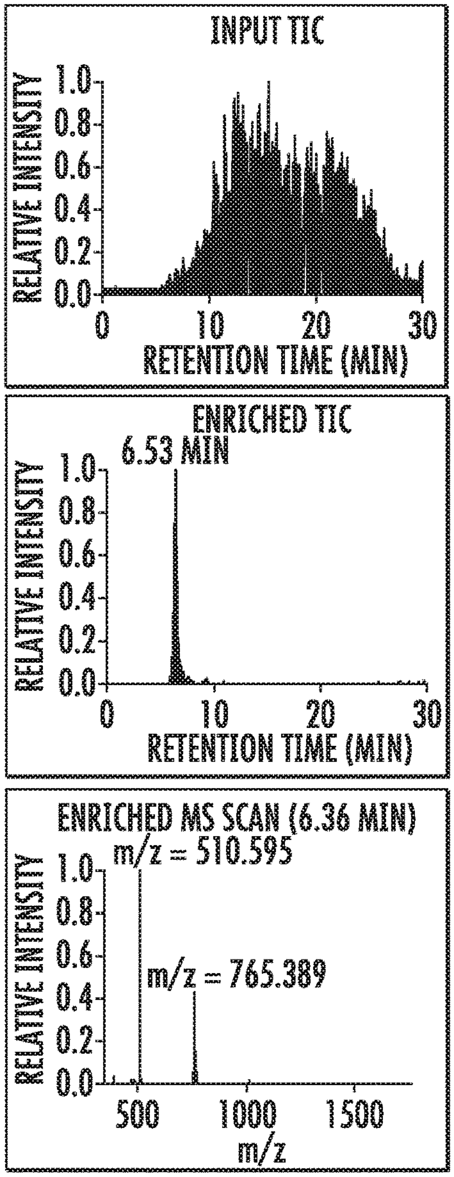
Figure 7D:
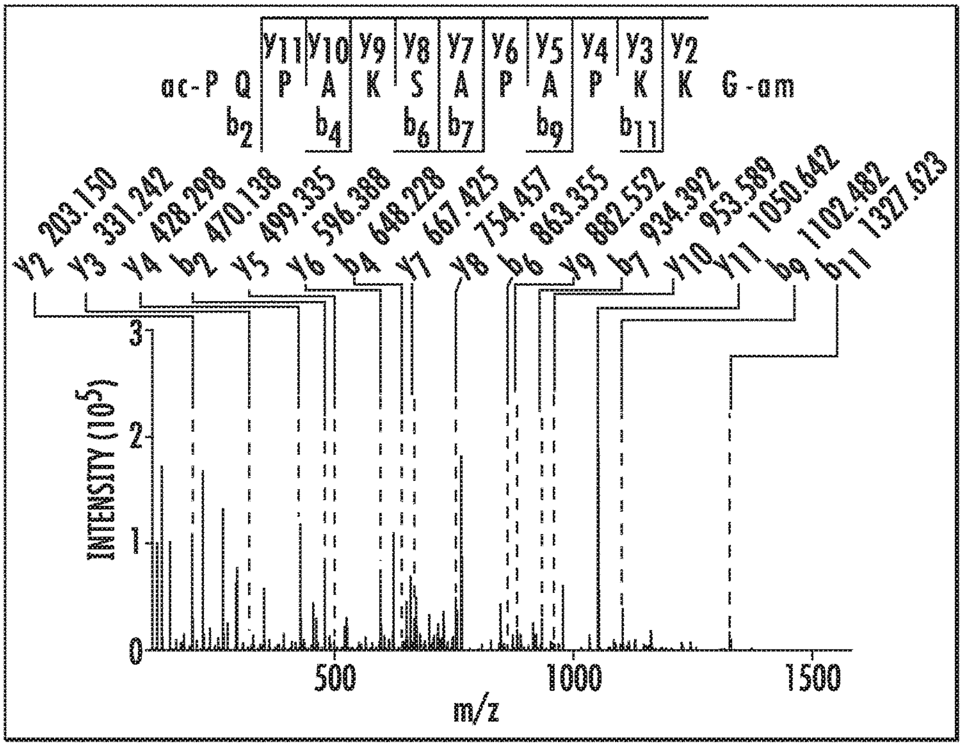
Figure 7E:
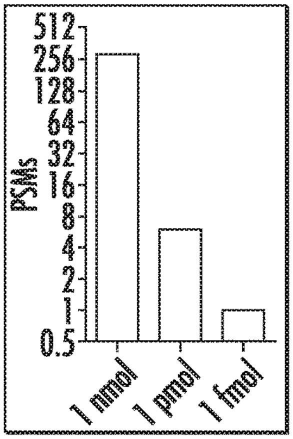
Figure 8A:
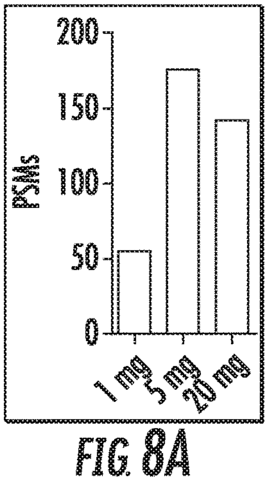
FIG. 8A-8F illustrates the identification of endogenous ADP-ribosylated substrates. Quantification of (a) PSM and (b) MaxQuant Score of ADP-ribosylated peptide identified from 1 mg, 5 mg and 20 mg HeLa cell lysate from DNA damage condition ($H_2O_2$). The distribution of site localization probability and ADP-ribosylated amino acid are presented in panel c and d. Examples of MS/MS spectra of endogenous (e) POP1 ADP-ribosylated Ser 24 and (f) hnRNPU Lysine 814.
Figure 8B:
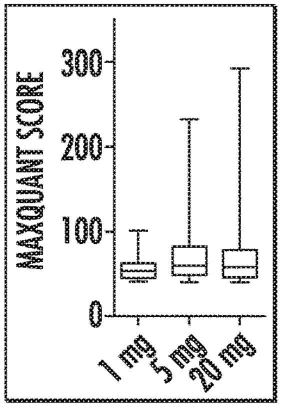
Figure 8C:
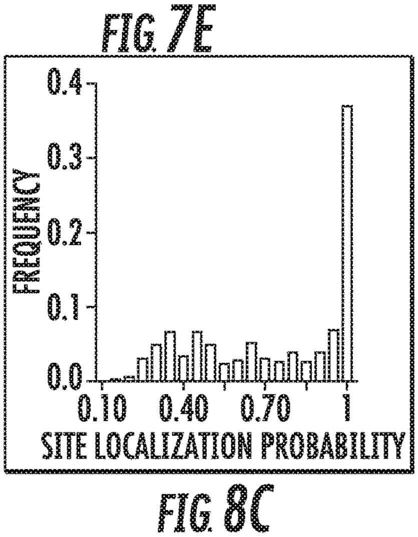
Figure 8D:
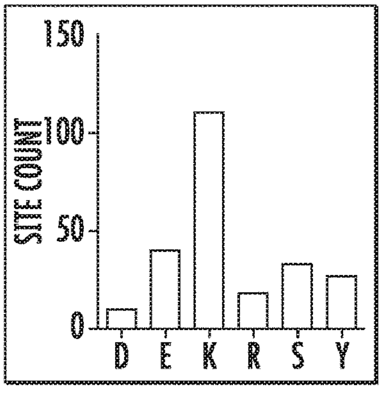
Figure 8E:
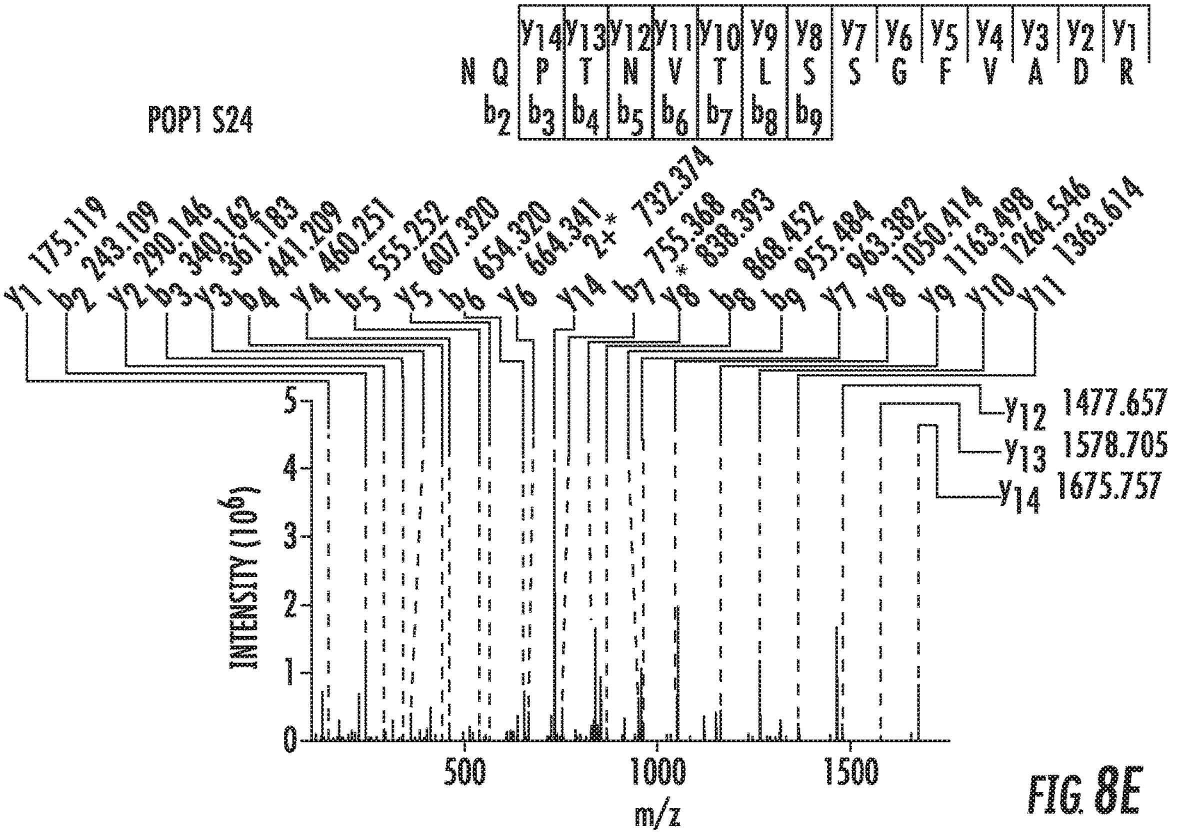
Figure 8F:
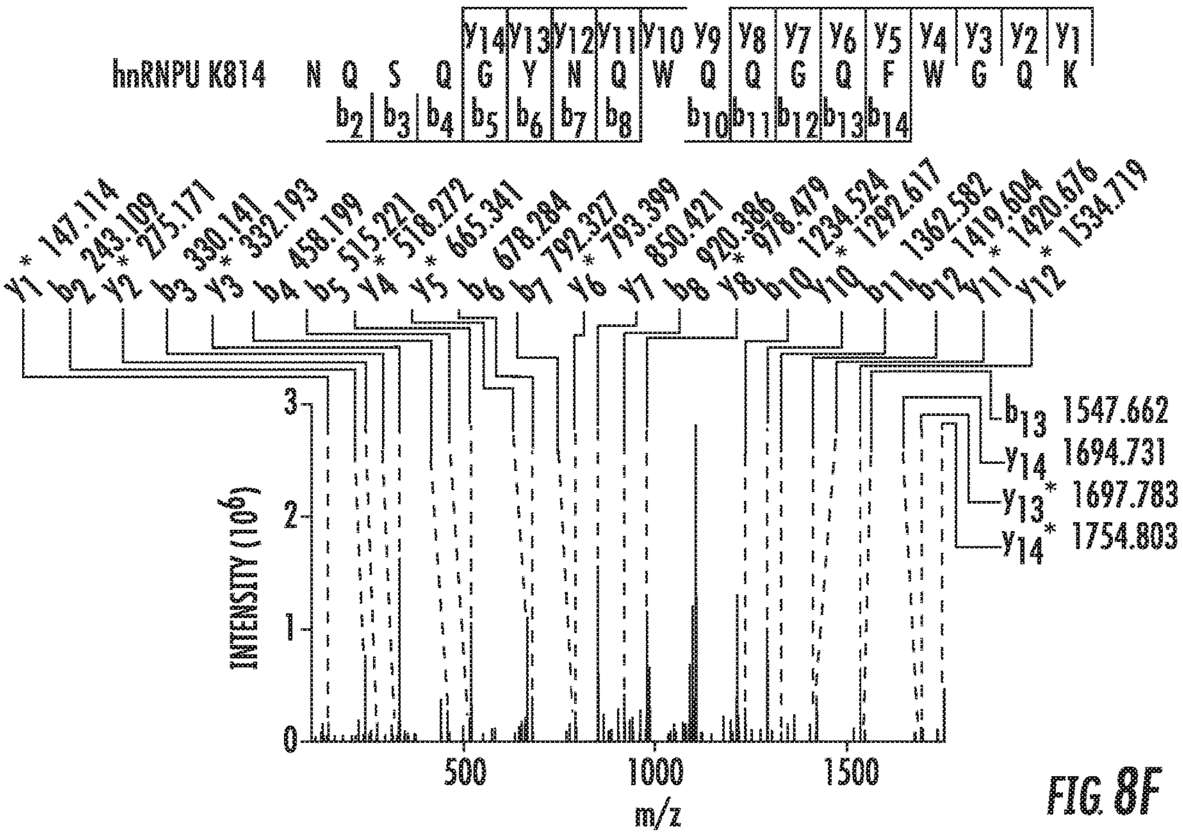

Next, the inventors assessed the robustness of this workflow in cell lysate to determine if it could be applied to enrich for and identify endogenous ADP-ribosylated substrates by liquid chromatography tandem mass spectrometry (LC-MS/MS). The inventors spiked 1 nmol of HK533 into 1 mg of a tryptic digest of HeLa cell lysate and used this complex peptide mixture as the input for the workflow. LC-MS/MS analysis of the input and eluent demonstrated that the workflow resulted in the robust enrichment of molecular species with a retention time of approximately 6.5 min (FIG. 7*c*, panels 1 and 2). MS analysis of this peak demonstrated that it was predominantly composed of two species that matched the expected m/z for phosphoribosylated HK533 in the +2 and +3 charge states (FIG. 7*c*, panel 3). Subsequent MS/MS analyses confirmed the sequence and site localization of HK533 (FIG. 7*d*). The inventors then applied this workflow to identify endogenous sites of ADP-ribosylation from cells. The inventors induced ADP-ribosylation by treatment of HeLa cells with $H_2O_2$, followed by cell lysis, protein isolation and protease digestion to peptides. After desalting, the inventors used 5 mgs of peptides as input for the ELTA-based enrichment workflow and analyzed the eluents by high-resolution LC-MS/MS for ADP-ribosylated peptide. The inventors' MS analyses resulted in the identification of 180 endogenous ADP-ribosylated sites, where many of these ADP-ribosylated proteins have been identified in previous proteomics studies (FIG. 8)

The inventors discovered a novel enzymatic approach to label the 2' OH terminus of ADP-ribose monomer and polymers. Though it is possible to label ADP-ribose at 1" aldehyde[16], the current method requires a large amount of materials for good yield, a special setup for chemical reactions and takes multiple days compared with 2 hours for ELTA. In addition, ELTA has now made it possible for labeling ADP-ribose that is conjugated to protein at 1" position (cf. FIG. 1*a*). Given OAS1 can use a range of dATP analogs, ELTA can serve as a research platform being applied to various techniques commonly used in molecular biology labs that require the derivation of the assayed molecule (e.g., radioactive, fluorescent, biotinylated, etc.). The inventors have demonstrated several proof-of-concept applications: (1) the use of fluorescently labeled PAR of defined chain length for biophysical measurements; (2) radiolabelling of PAR isolated from cells allows the assessment of polymer length; (3) the use of an azide tag to directly conjugate ADP-ribosylated peptides onto agarose bead for enrichment of ADP-ribosylated substrates for mass spectrometry identification. The inventors noted that the azido labeling also allows us to tap into the versatility of click chemistry for bioconjugation to any compatible substrates. Given that the synthetic routes of various ATP derivatives have already been established[44], it is foreseeable that similar dATP analogs can be made and applied to ELTA for new applications. For example, adding fluorine-19 for making an NMR probe or a diazirine group for a photoaffinity probe. On the other hand, an additional use of ATP analog may allow signal amplification. When combined with the existing chemical approach to label PAR at 1" position, we can now attach functionality at both termini. Such dual labeling approach has been transformative for investigating DNA and RNA biology, and, therefore, ELTA may now open the possibility for PAR to serve as a building block in synthetic biology (e.g., creating model substrates with a defined length of PAR). In addition, given that ELTA labels 2'-OH terminus and that some PARPs create branchpoints resulting in additional 2'-OH groups from a single 1" terminus, labeling at both 1" and 2' ends may determine the branching frequency of intact PAR polymer isolated in vitro or from cells.

Currently, ELTA can effectively label femtomole levels of ADP-ribose in a complex background, thereby allowing for efficient labeling of limited materials for downstream analyses. The inventors have demonstrated the use of fluorescent PAR of defined length for measurement of the equilibrium dissociation constant with a PAR-binding module using ITC and MST, but these labeled molecules can also be used for single molecule-based measurement[45] or intracellular tracking of PAR. Several methods have been developed to measure the length of PAR chain from cells; however, the majority of them requires the digestion of PAR into monomeric nucleosides prior to analyses, thereby losing the information of length distribution of intact PAR chain. Alternatively, it is possible to measure the length of intact PAR chain from cells by feeding radiolabeled adenine. However, this approach suffers several drawbacks, including non-specific labeling of other polynucleotides (DNA and RNA) and potential induction of PAR signals by the radiodamage of DNA. Using ETLA, we found that PAR length distribution reduced significantly in $H_2O_2$-treated cells by PARP inhibitors and, unexpectedly, the accumulation of shorter PAR upon PARG inhibition, which might have therapeutic implications. Notably, FDA-approved PARP inhibitors Niraparib and Olaparib accumulate DNA damage only when PAR level is reduced down to >90%. One possible interpretation is that a longer PAR chain can still result in DNA repair, but not with a shorter one, consistent with the previous observation that DNA repair factors bind to PAR in a length-selective manner. Therefore, it will be interesting to explore whether PAR length distribution could be an important biomarker for clinical effectiveness of these inhibitors.

The inventors demonstrated that ELTA labels free and protein-conjugated ADP-ribose as well as several examples of its applications. However, this novel technique may have broader applications on ADP-ribose metabolism or adenosine-containing molecules that possess free 2'OH terminus. Besides protein-conjugated ADP-ribose, studies in prokaryotes and eukaryotes have revealed several ADP-ribose derivatives, including O-acetyl-ADP-ribose by the sirtuin deacetylase family, ADP-ribose-1"-phosphate from tRNA splicing. ADP-ribosylation of the antibiotics rifamycin, as well as the recently discovered DNA ADP-ribosylation. In humans, ADP-ribosylation is catalyzed by poly(ADP-ribose) polymerases (PARPs), which consists of 17 members PARPs covalently attach the ADP-ribose (ADPR) unit to all polar residues, including asparate, glutamate, serine, cysteine, lysine, arginine, histidine and tyrosine. However, most of them are only able to transfer single mono(ADP-ribose) (MAR) group onto their target proteins. To date PARP1, 2, and 3 have been identified to catalyze PARylation during DNA damage response (DDR). In addition, tankyrases including tankyrase-1 (PARP5a) and lanky rase-2 (PARP5b) have also been shown to contribute to genomic stability. Among these PARPs, PARP1 is the founding member of PARP family for the synthesis of PAR chains. The mechanism of PARP1 activation by single-strand and double-strand DNA breaks (SSBs and DSBs) is well established. Using $NAD^+$ as substrate, PARPs repeatedly catalyze the transfer of successive units of ADPR moieties via a unique 2',1"-O-glycosidic ribose-ribose bond to target proteins, finally producing PAR chain. Several reports have demonstrated that PAR chains can comprise up to 200 ADPR units in length. In addition, PARP1 can introduce branching into PAR chains through the 2',1"-glycosidic bond.

Figure 9:
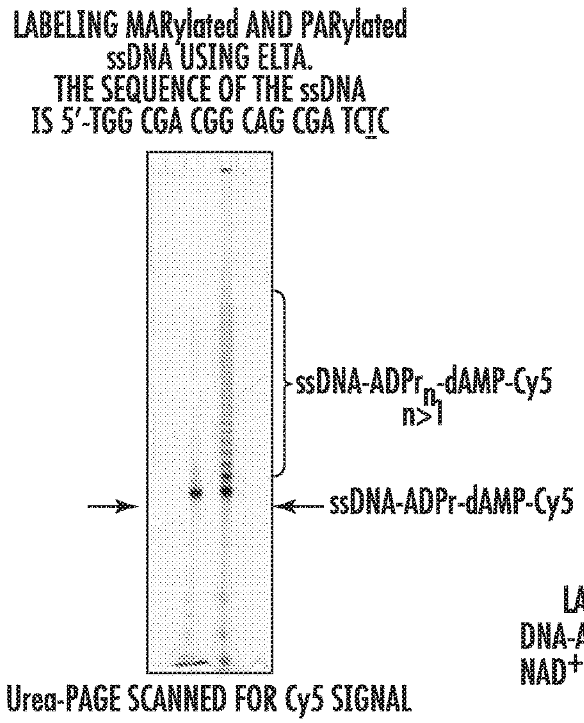
FIG. 9 illustrates labeling MARylated and PARylated ssDNA using ELTA. DNA-PAR-Cy5 separated using Urea-PAGE (15%) and visualized by scanning for Cy5 signal using phosphoimager. Sequence of ssDNA is TGG CGA CGG CAG CGA TCTC. Same condition was used to label MARylated and PARylated DNA.
Figure 10:
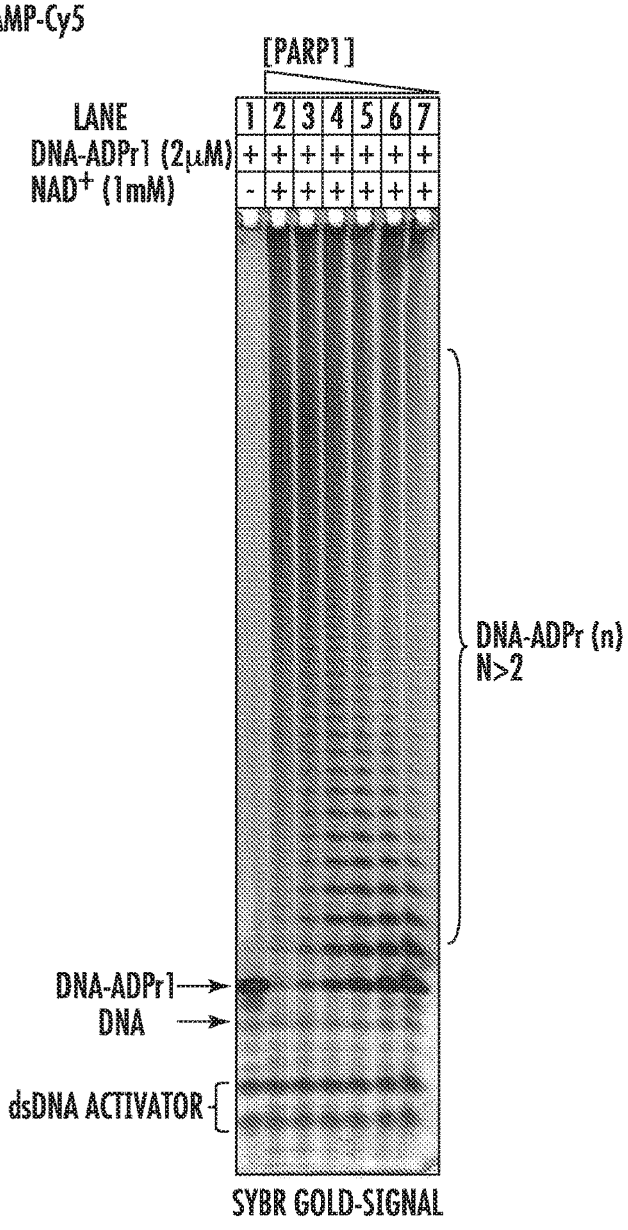
FIG. 10 illustrates human PARP1 (hPARP1) catalyzes the ADP-ribosylation of MARylated DNA in concentration-dependent manner. Decreasing hPARP1 concentration shifts PARylation profile to shorter length of PAR as shown in on Urea-PAGE (15%). Concentration of hPARP1 is decreasing from lane 2 to 7 from 2.8 to 0.1 μM. Sequence of ssDNA is TGG CGA CGG CAG CGA TCTC. Gel is visualized using SYBR gold and all reaction contains PARylation buffer, dsDNA activator, spermine.

To illustrate the ability of ELTA to labeled MARylated and PARylated DNA, the inventor made MARylated DNA using the bacterial toxin DarT, which modifies the second thymidine in a single stranded DNA containing a TNTC motif. The inventor also developed a novel protocol to make PARylated DNA by incubating MARylated DNA with the human enzyme PARP1. $NAD^+$, double-stranded DNA and spermine. The MARylated and PARylated DNA were both labeled by ELTA (FIGS. 9 and 10). ELTA may, therefore, provide a timely tool for discovering the functions of these various forms of ADP-ribosylation in antibiotic resistance, as well as $NAD^+$, RNA and DNA metabolism.

Kits

Any of the compositions described herein may be comprised in a kit. In a non-limiting example, labeled ADP-ribose/PAR, 2'OH labelling enzyme such as OAS, and/or a label, may be comprised in a kit.

The kits may comprise a suitably aliquoted of these components and, in some cases, one or more additional agents. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the compositions of the present invention and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The composition(s) of the present invention may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of labeling ADP-ribose comprising:

providing a monomer or polymer of ADP-ribose; and incubating the monomer or polymer of ADP-ribose with an enzyme and a label;

forming a monomer or polymer of ADP-ribose labeled at the 2'OH terminus, wherein the enzyme is a 2'-5'-Oligoadenylate Synthetase (OAS) selected from the group consisting of OAS1, OAS2, OAS3, and 2'-5' Oligoadenylate Synthetase-Like protein (OASL), and wherein the label comprises a Cy3 moiety, a Cy5 moiety, a Biotin moiety, an Azido moiety, and/or a $^{32}P$ moiety.

2. The method of claim 1 wherein the ADP-ribose is a monomer.

3. The method of claim 1 wherein the ADP-ribose is a polymer.

4. The method of claim 1 wherein the polymer of ADP-ribose has 100 or more ADP-ribose subunits.

5. The method of claim 1 wherein the polymer of ADP-ribose has less than 100 ADP-ribose subunits.

6. The method of claim 1 wherein the label is a compound having formula VII:

(VII)

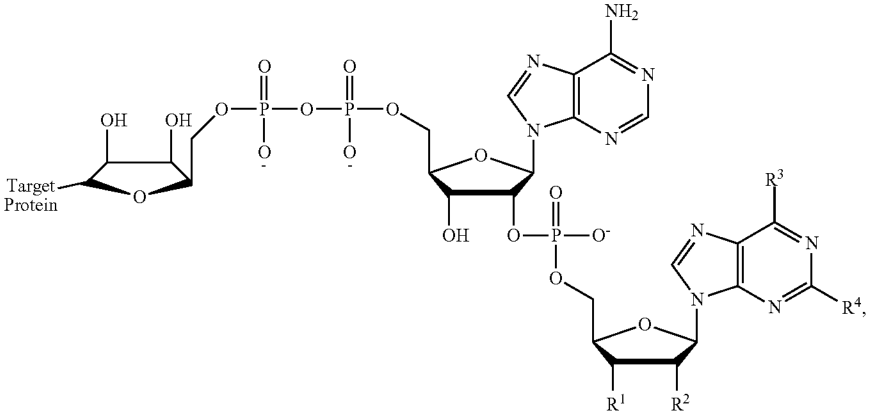

wherein $R^1$ is OH or any group selected from the following:

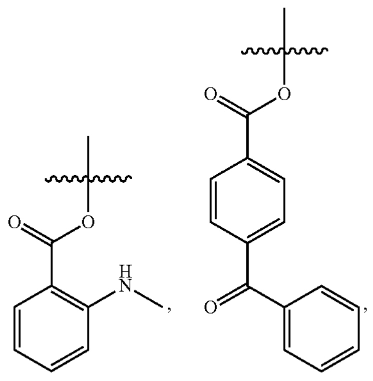

mant- BZ$_2$-

-continued
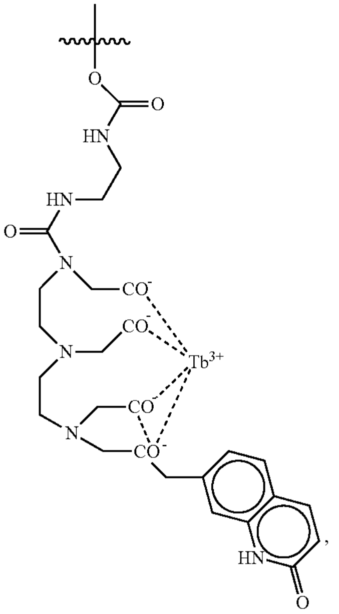
Tb-chelate-EDA-
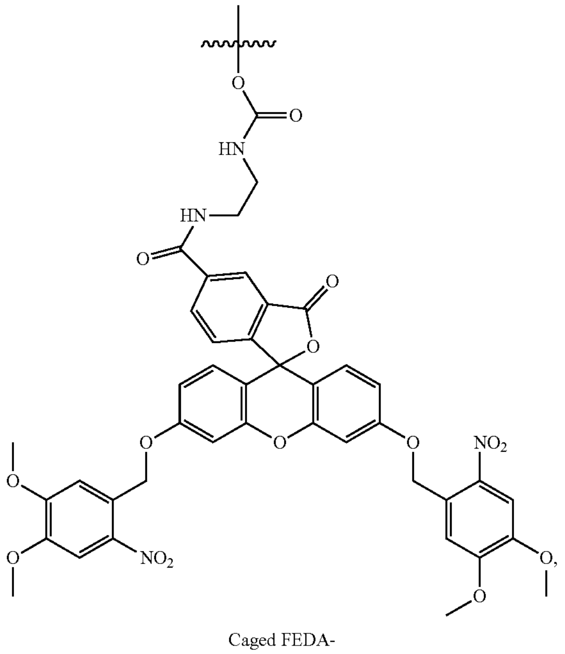
Caged FEDA-
-continued
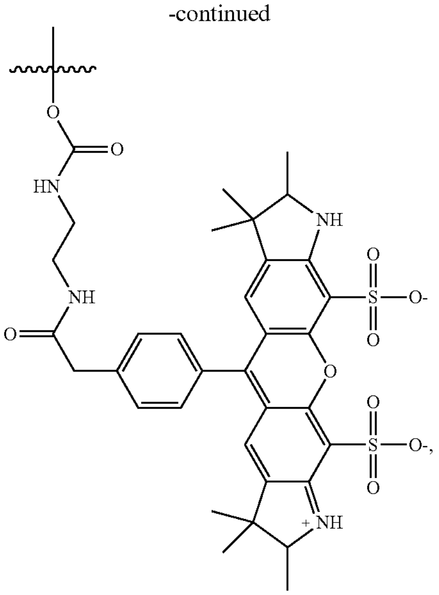
Alex[523]-EDA-
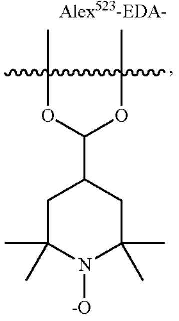
or
2′,3′-TEMPO-
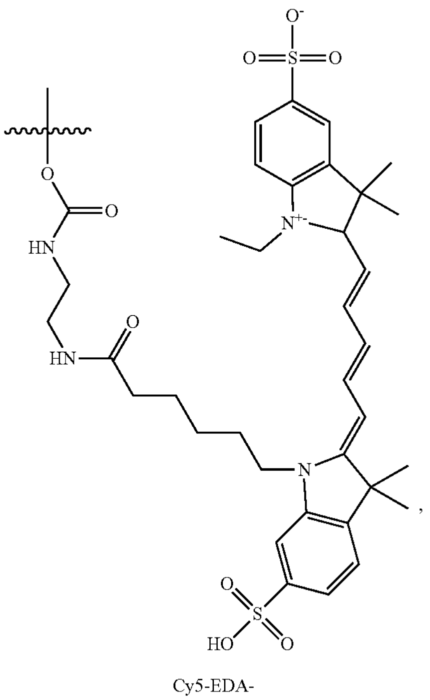
Cy5-EDA- $R^2$ is H or OH or any group selected from the following:
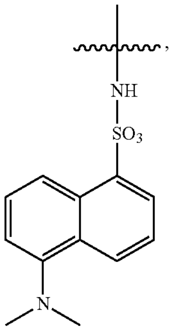
, or
2′-DNS-
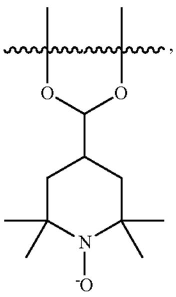
2′,3′-TEMPO-
$R^3$ is $NH_2$ or any group selected from the following:
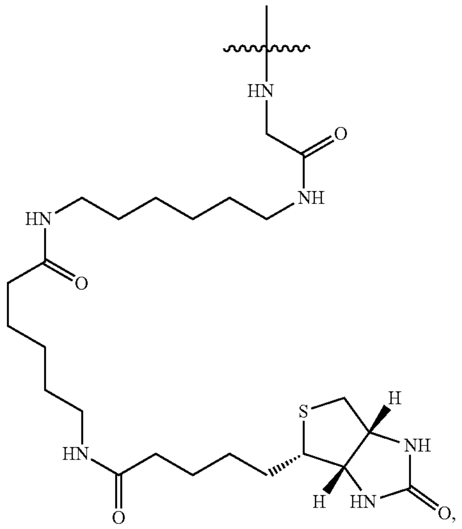
Biotin-17-
-continued
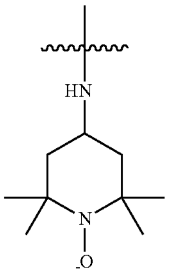
, or
TEMPO-$N^6$-
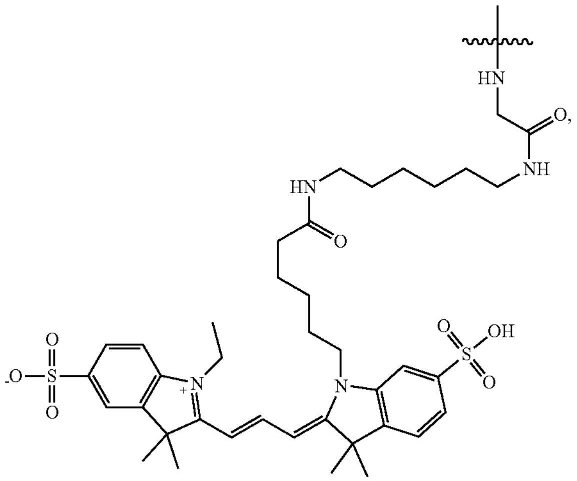
Cy3-$N^6$-
and $R^4$ is F or Cl.

7. The method of claim 1 wherein the monomer or polymer of ADP-ribose labeled at the 2'OH terminus having the structure of Formula I:

(I)

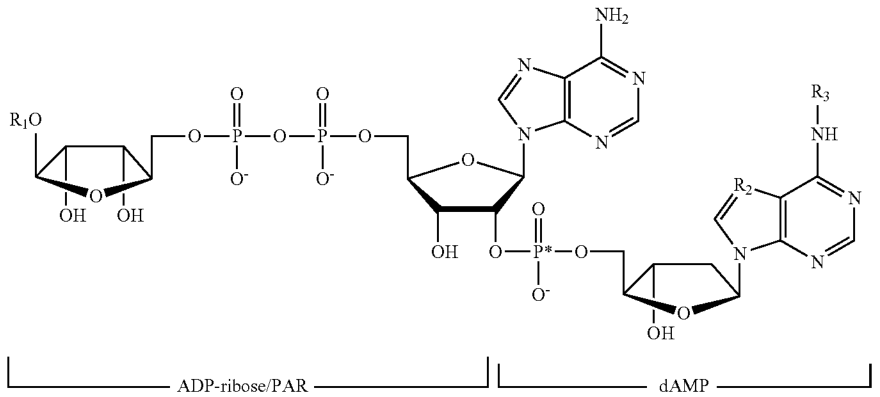

wherein R1 is H or (ADP-ribose) n, wherein n≥1; R2 is N, N linked to the Cy3 moiety, or N linked to the Cy5 moiety; and R3 is H, the Cy5 moiety, the Biotin moiety, or the Azido moiety; and where P* is P or the $^{32}P$ moiety.

8. The method of claim 1 wherein the monomer or polymer of ADP-ribose labeled at the 2'OH terminus having the structure of Formula V:

ADP-ribose/poly(ADP-ribose)(PAR)-X (V)

wherein X is a label of Formula VII:

(VII)

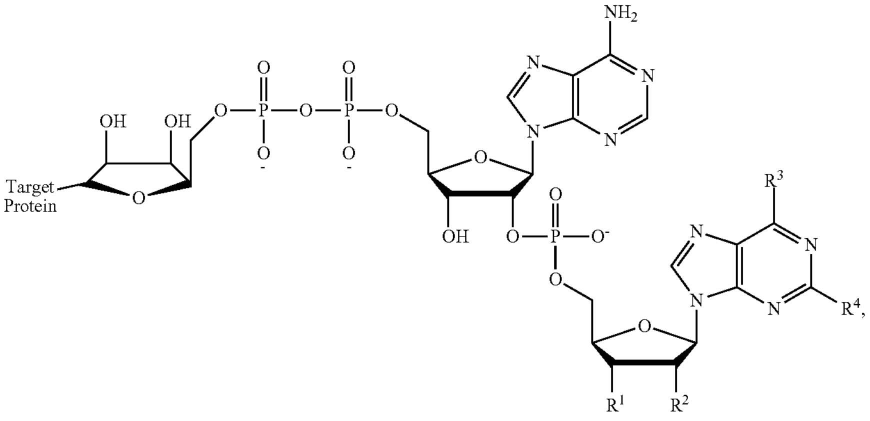

wherein $R^1$ is OH or any group selected from the following:
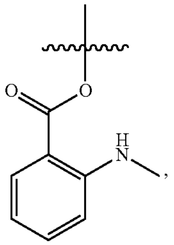
mant-
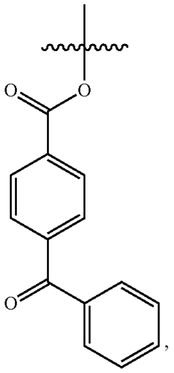
$BZ_2$-
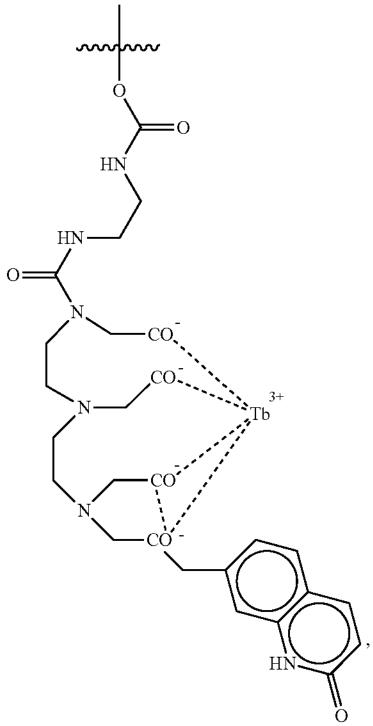
Tb-chelate-EDA-
-continued
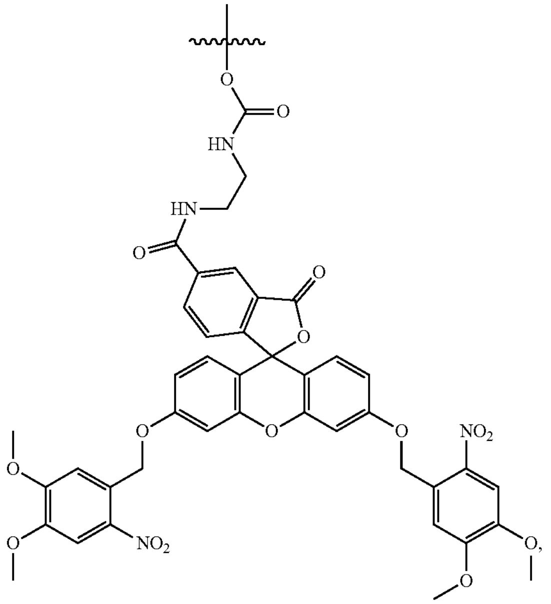
Caged FEDA-
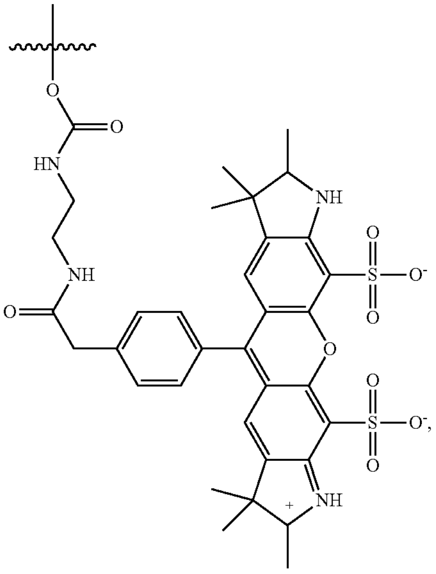
$Alex^{532}$-EDA-
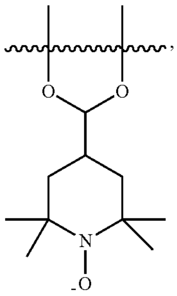
or
2′,3′-TEMPO-

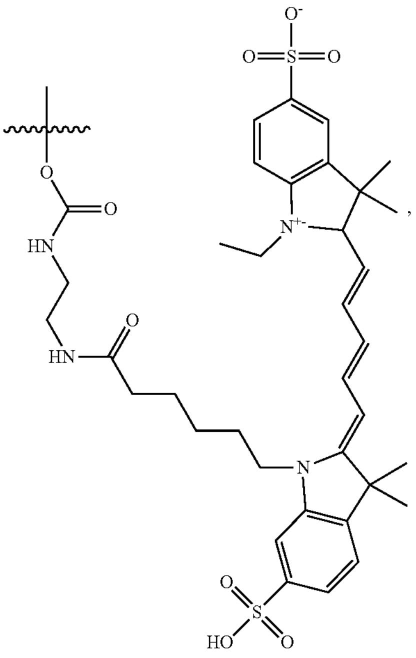
Cy5-EDA-
$R^2$ is H or OH or any group selected from the following:
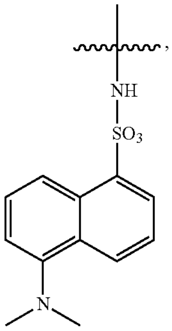
, or
2′-DNS-
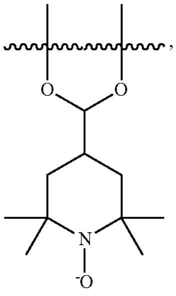
,
2′,3′-TEMPO-
$R^3$ is $NH_2$ or any group selected from the following:
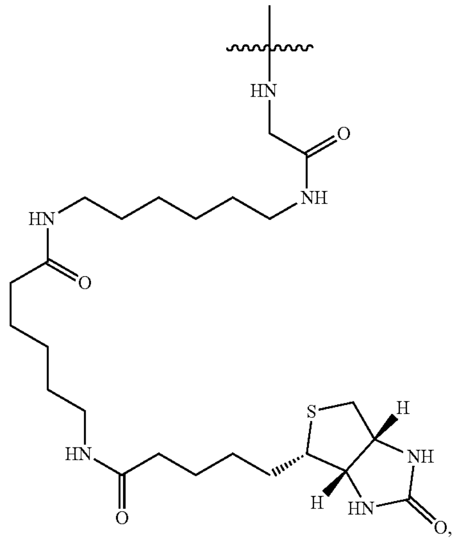
Biotin-17-
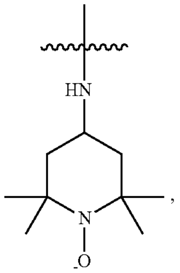
, or
TEMPO-N6-
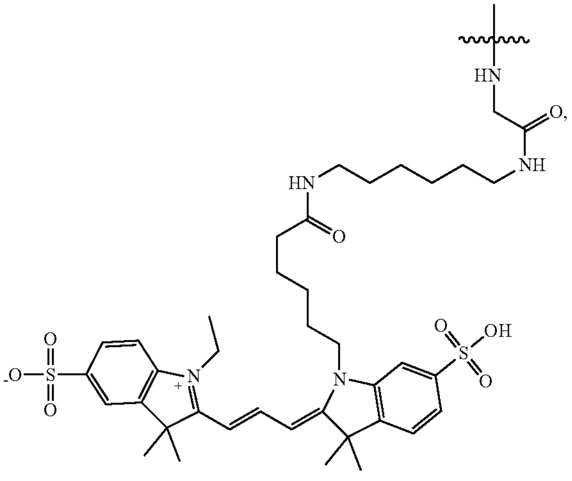
Cy3-N6- and $R^4$ is F or Cl.

9. The method of claim 1 providing the monomer or polymer of ADP-ribose is in vitro.

10. The method of claim 1 providing the monomer or polymer of ADP-ribose is in vivo.

11. A method of labeling ADP-ribose comprising:
providing a protein attached to a monomer or a polymer of ADP-ribose;
incubating the protein attached to a monomer or a polymer of ADP-ribose with an enzyme and a label;
forming a protein attached to the monomer or polymer of ADP-ribose labeled at the 2'OH terminus,
wherein the enzyme is a 2'-5'-Oligoadenylate Synthetase (OAS) selected from the group consisting of OAS1, OAS2, OAS3, and 2'-5' Oligoadenylate Synthetase-Like protein (OASL), and
wherein the label comprises a Cy3 moiety, a Cy5 moiety, a Biotin moiety, an Azido moiety, and/or a $^{32}P$ moiety.

12. The method of claim 11 wherein the protein is attached to a monomer of ADP-ribose.

13. The method of claim 11 wherein the protein is attached to a polymer of ADP-ribose.

14. The method of claim 11 wherein the polymer of ADP-ribose has 100 or more ADP-ribose subunits.

15. The method of claim 11 wherein the polymer of ADP-ribose has less than 100 ADP-ribose subunits.

16. The method of claim 11 wherein the label is a compound having formula VII:

(VII)

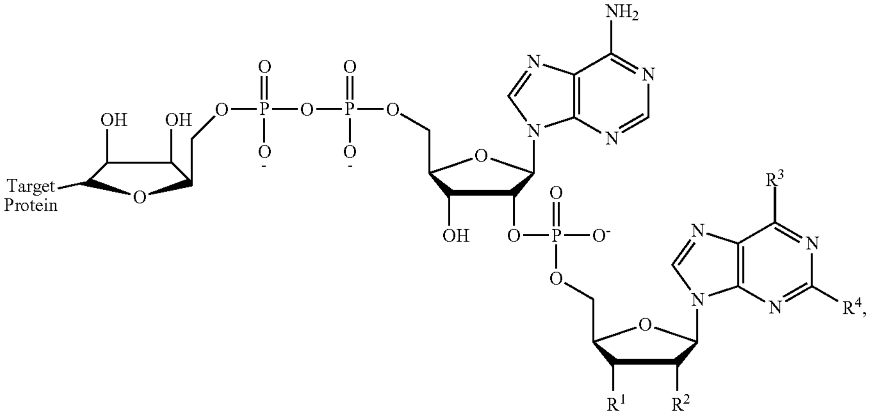

- wherein $R^1$ is OH or any group selected from the following:

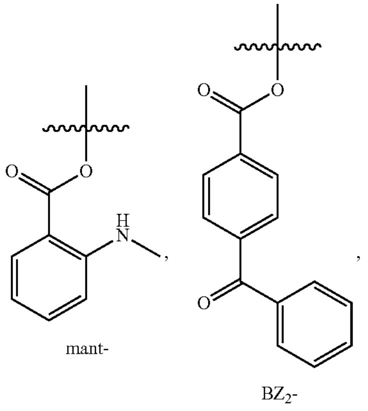

-continued
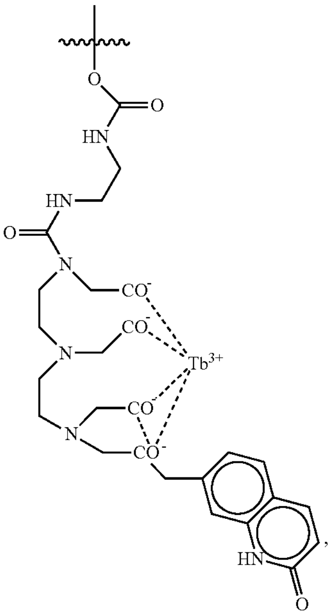
Tb-chelate-EDA-
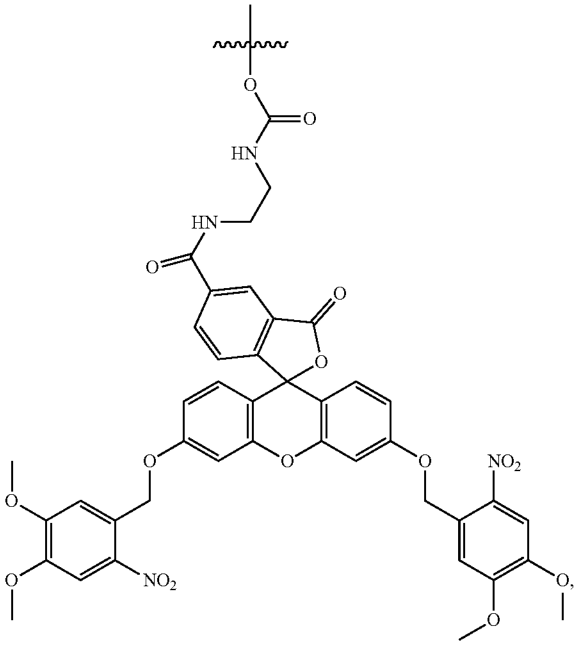
Caged FEDA-
-continued
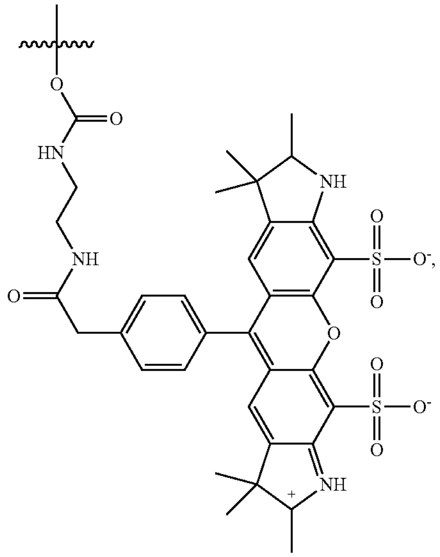
Alex532-EDA-
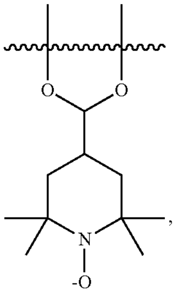
2′,3′-TEMPO-
or
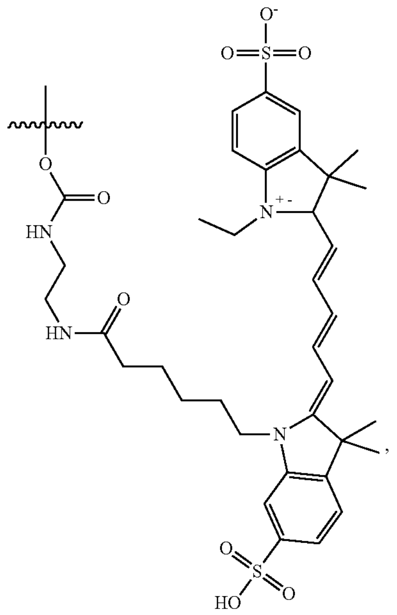
Cy5-EDA- $R^2$ is H or OH or any group selected from the following:
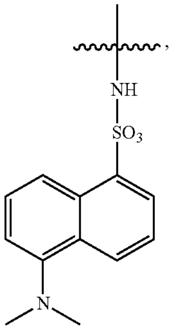
, or
2'-DNS-
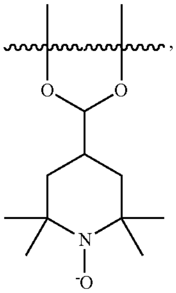
,
2',3'-TEMPO-
$R^3$ is $NH_2$ or any group selected from the following:
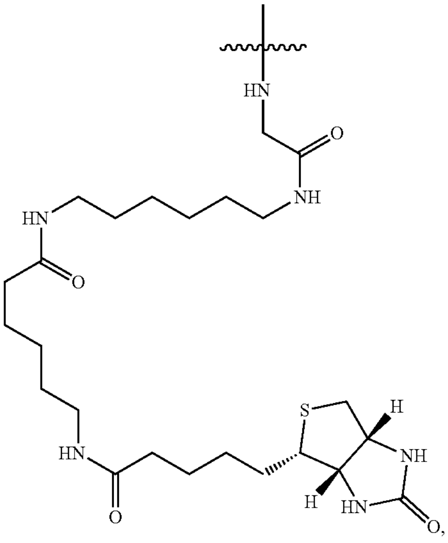
,
Biotin-17-
-continued
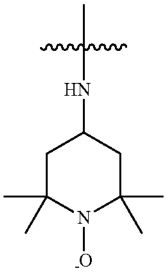
, or
TEMPO-N$^6$-
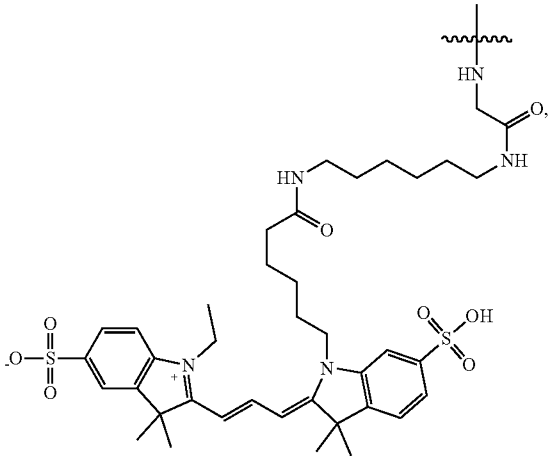
,
Cy3-N$^6$-
and $R^4$ is F or Cl.
17. The method of claim 11 wherein the protein attached to the monomer or the polymer of ADP-ribose labeled at the 2'OH terminus having the structure of formula II, formula III, or formula IV:

(II)
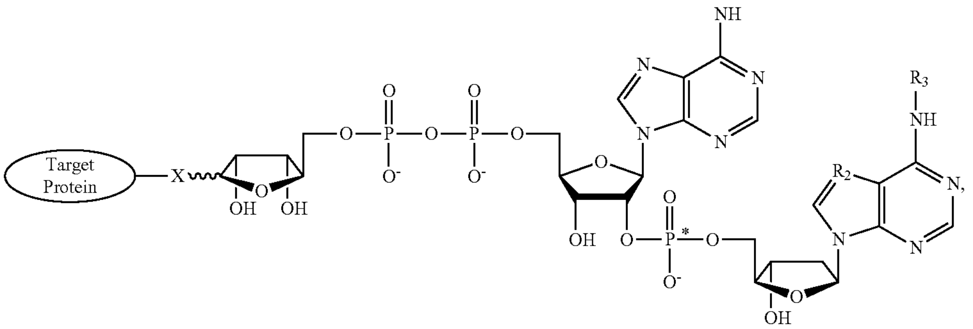
Mono(ADP-ribosyl)ated protein
(III)
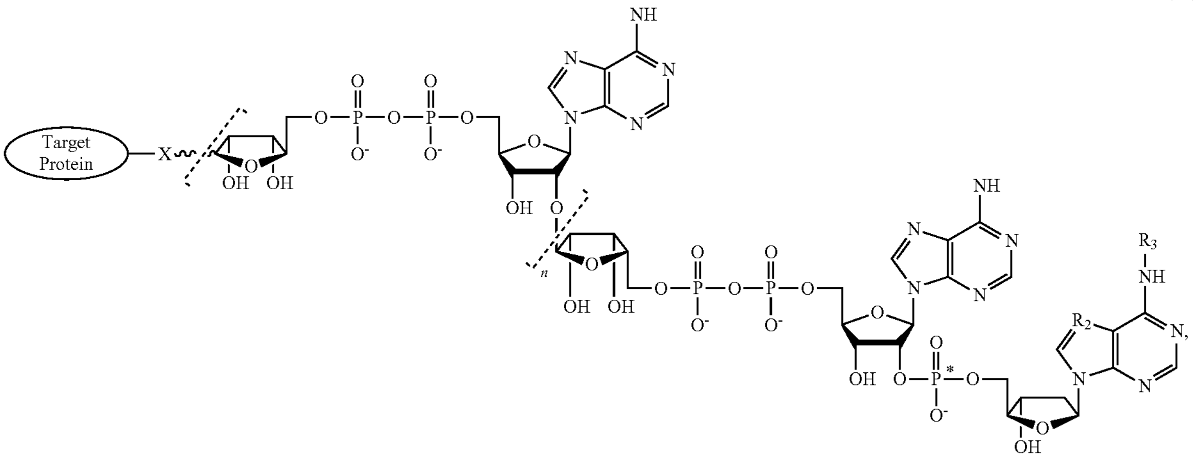
Poly(ADP-ribosyl)ated protein (with linear chain)
(IV)
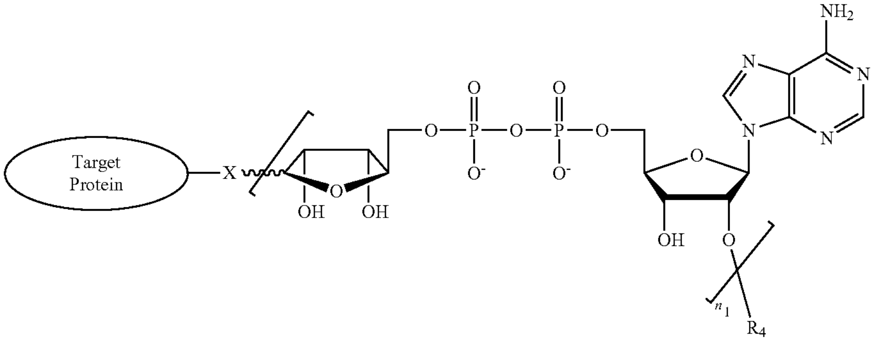
Poly(ADP-ribosyl)ated protein (with branched chain)

wherein X is O (Asp, Glu, Ser), N (Lys, Arg, Asn, Dph), or S (Cys), R2 is N, N linked to the Cy3 moiety, or N linked to the Cy5 moiety; R3 is H, a Cy5, a Biotin, or an Azido moiety; R4 is
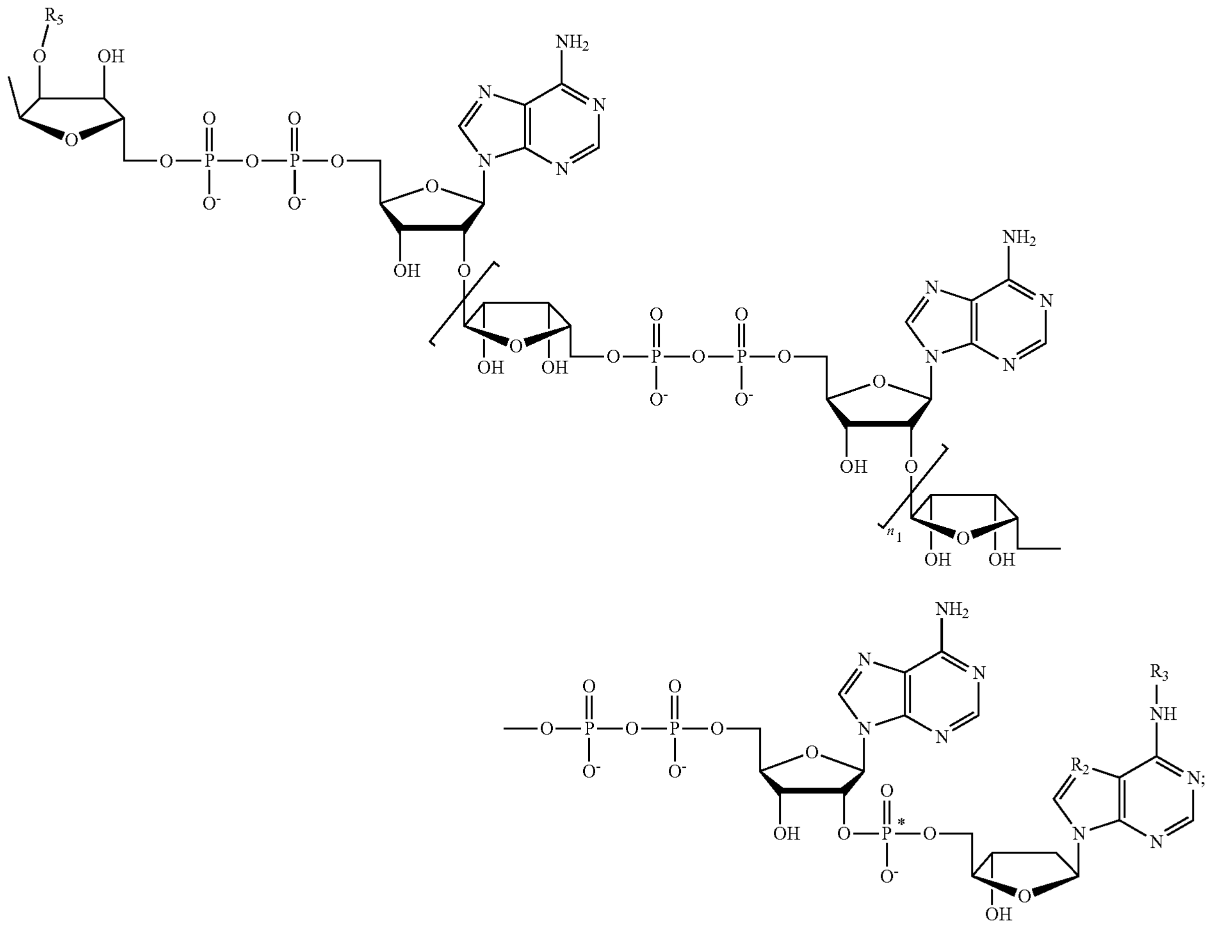
R5 is
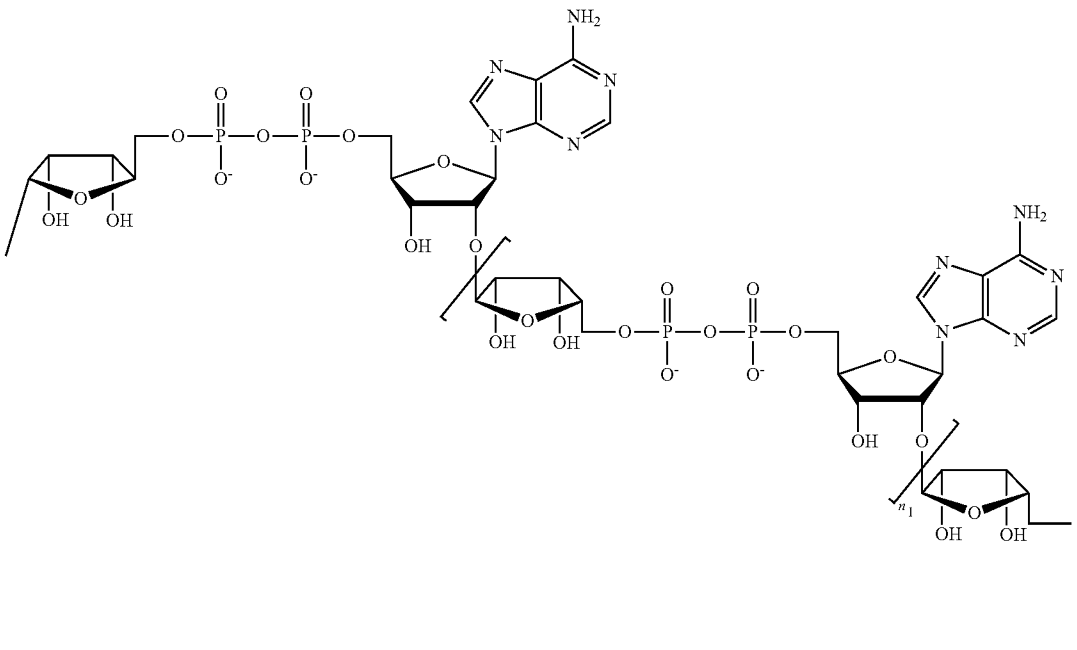

-continued
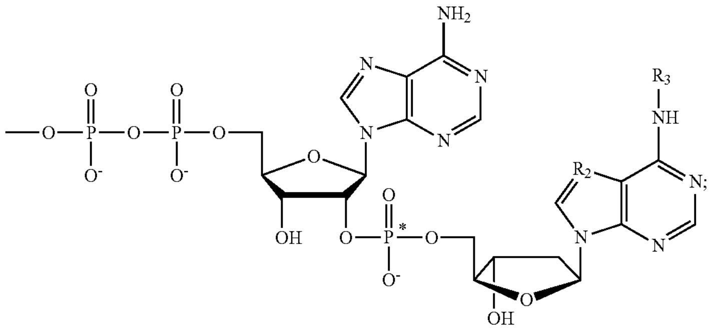
and where P* is P or $^{32}P$.
18. The method of claim 11 wherein the protein attached to the monomer or polymer of ADP-ribose labeled at the 2'OH terminus having the structure of Formula VI:
Target Protein-ADP-ribose/poly(ADP-ribose)(PAR)-X/PAR X (VI)
wherein X is the label of Formula VII:
(VII)
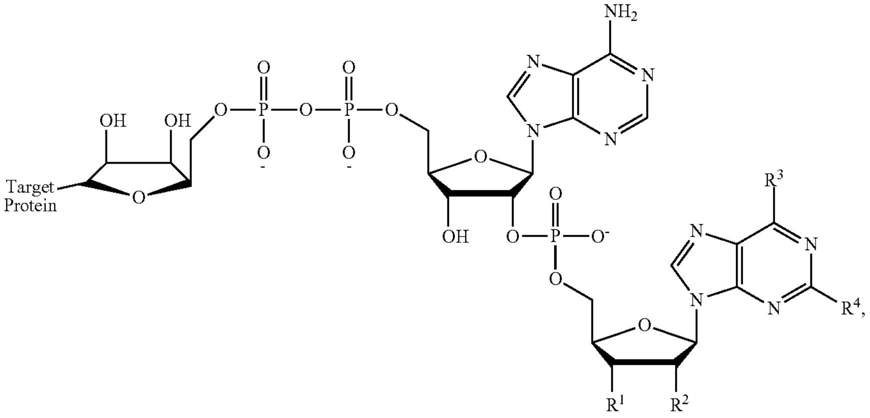
wherein $R^1$ is OH or any group selected from the following:
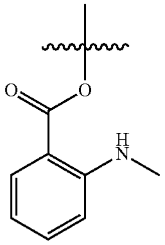
mant- ,
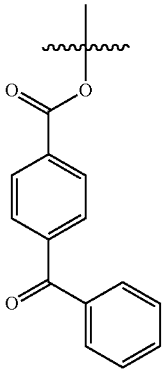
$BZ_2$- , -continued
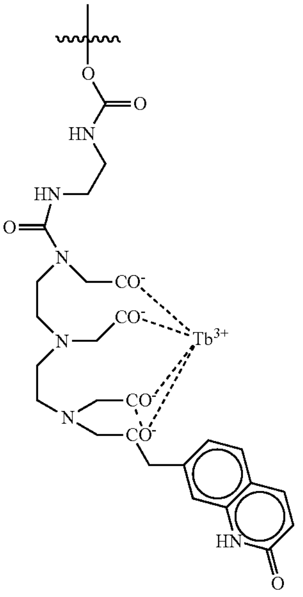
Tb-chelate-EDA- ,
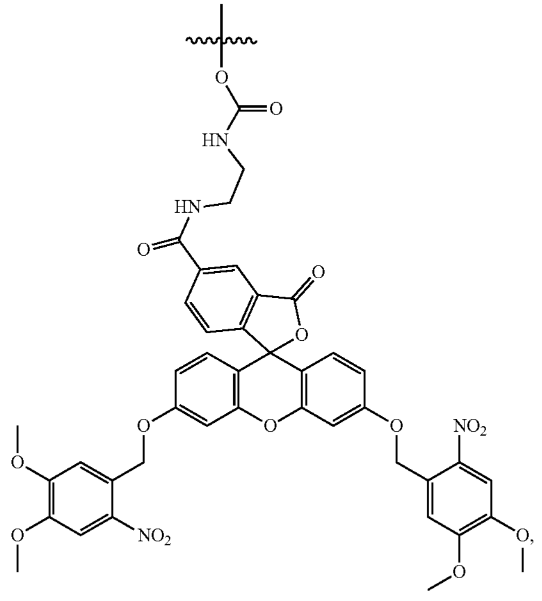
Caged FEDA-
-continued
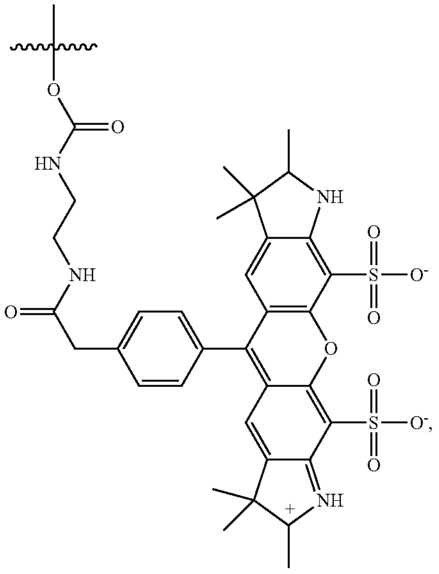
Alex$^{532}$-EDA-
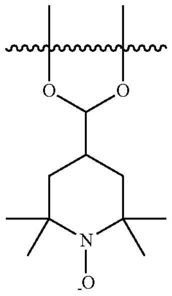
2′,3′-TEMPO- , or
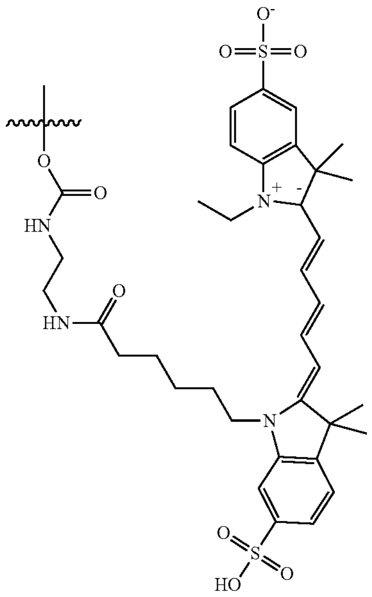
Cy5-EDA- , $R^2$ is H or OH or any group selected from the following:

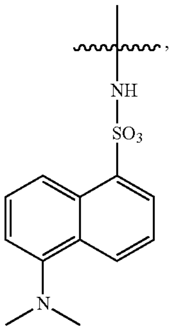

, or

2'-DNS-

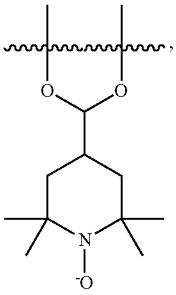

,

2',3'-TEMPO- $R^3$ is $NH_2$ or any group selected from the following:

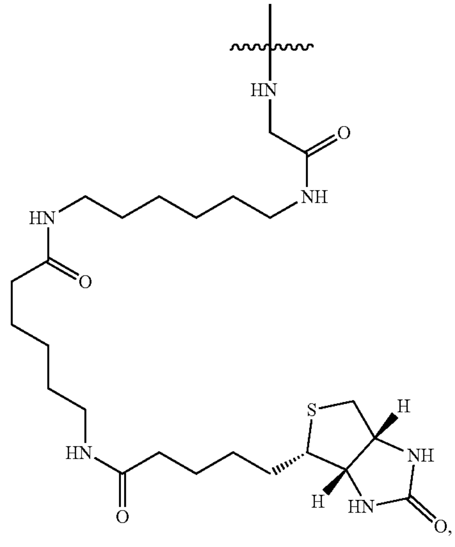

,

Biotin-17-

-continued

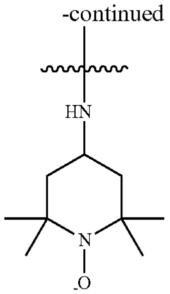

TEMPO-$N^6$- , or

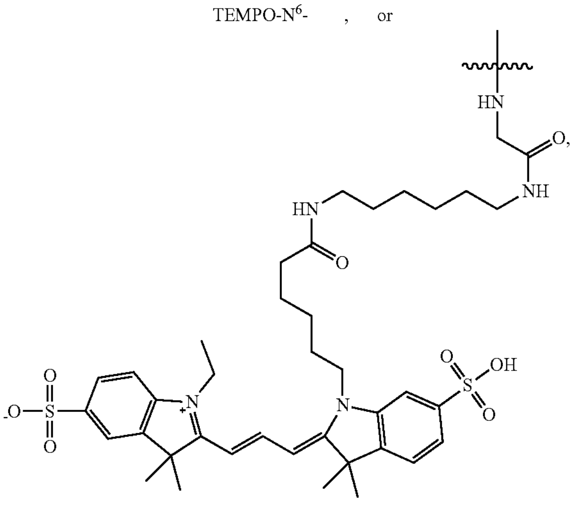

,

Cy3-$N^6$- and $R^4$ is F or Cl.

19. The method of claim 11 providing an in vitro protein attached to the monomer or the polymer of ADP-ribose.

20. The method of claim 11 providing an in vivo protein attached to the monomer or the polymer of ADP-ribose monomer.

21. A method of identifying a protein ADP-ribose conjugation site comprising the steps of:

providing a protein attached to a monomer or polymer of ADP-ribose;

incubating the cellular proteins with an enzyme that attaches a label at the 2'OH terminus of the monomer or polymer of ADP-ribose wherein the label binds to a separation agent, wherein the enzyme is a 2'-5'-Oligoadenylate Synthetase (OAS) selected from the group consisting of OAS1, OAS2, OAS3, and 2'-5' Oligoadenylate Synthetase-Like protein (OASL), and wherein the label comprises a Cy3 moiety, a Cy5 moiety, a Biotin moiety, an Azido moiety, and/or a $^{32}P$ moiety;

forming a labeled protein;

binding the labeled protein to a separation agent;

purifying the labeled protein;

identifying a protein ADP-ribose binding site on the labeled protein.

22. A method of labeling a polymer comprising the steps of:

providing a polymer comprising an ADP-ribose;

incubating the polymer with an enzyme and a label; and forming a polymer comprising an ADP-ribose labeled at the 2'OH terminus, wherein the enzyme is a 2'-5'-Oligoadenylate Synthetase (OAS) selected from the group consisting of OAS1, OAS2, OAS3, and 2'-5' Oligoadenylate Synthetase-Like protein (OASL), and wherein the label comprises a Cy3 moiety, a Cy5 moiety, a Biotin moiety, an Azido moiety, and/or a $^{32}P$ moiety.

23. The method of claim 22 wherein the polymer is selected from the group consisting of a nucleic acid, a protein a peptide, a polymer of ADP-ribose, and a combination thereof.

24. The method of claim 22 wherein the polymer is a nucleic acid.

25. The method of claim 24 wherein the wherein the nucleic acid is single stranded.

26. The method of claim 24 wherein the nucleic acid is DNA.

27. The method of claim 24 wherein the nucleic acid is RNA.

28. The method of claim 22 wherein the polymer is a protein or peptide.

* * * * *